US012171821B2

(12) United States Patent
Knoll et al.

(10) Patent No.: US 12,171,821 B2
(45) Date of Patent: Dec. 24, 2024

(54) ***TOXOPLASMA GONDII* VACCINE**

(71) Applicant: Wisconsin Alumni Research Foundation (WARF), Madison, WI (US)

(72) Inventors: Laura Knoll, Madison, WI (US); Bruno Martorelli Di Genova, Madison, WI (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 818 days.

(21) Appl. No.: 17/251,121

(22) PCT Filed: Jun. 13, 2019

(86) PCT No.: PCT/US2019/037084
§ 371 (c)(1),
(2) Date: Dec. 10, 2020

(87) PCT Pub. No.: WO2019/241579
PCT Pub. Date: Dec. 19, 2019

(65) Prior Publication Data

US 2021/0121545 A1 Apr. 29, 2021

Related U.S. Application Data

(60) Provisional application No. 62/684,524, filed on Jun. 13, 2018.

(51) Int. Cl.
*A61K 39/002* (2006.01)
*A01K 67/027* (2024.01)

(52) U.S. Cl.
CPC .......... *A61K 39/002* (2013.01); *A01K 67/027* (2013.01); *A01K 2227/105* (2013.01)

(58) Field of Classification Search
None
See application file for complete search history.

(56) References Cited

U.S. PATENT DOCUMENTS 6,737,237 B1 * 5/2004 McLeod .............. A61K 39/002 435/254.2

FOREIGN PATENT DOCUMENTS

| | | | |
|---|---|---|---|
| CN | 105296356 | A | 2/2016 |
| EP | 0687471 | A1 | 12/1995 |
| EP | 0700991 | A1 | 3/1996 |
| WO | WO-2016144933 | A1 | 9/2016 |
| WO | WO-2019241579 | A1 | 12/2019 |

OTHER PUBLICATIONS

Lunden et al (Infect. Immun., 61:26392643, 1993).*
"International Application Serial No. PCT/US2019/037084, International Search Report mailed Nov. 14, 2019", 10 pgs.
"International Application Serial No. PCT/US2019/037084, Invitation to Pay Add'l Fees and Partial Search Report mailed Sep. 24, 2019", 10 pgs.

(Continued)

*Primary Examiner* — Brian Gangle
(74) *Attorney, Agent, or Firm* — Schwegman Lundberg & Woessner, P.A.

(57) ABSTRACT

Methods of preparing mammalian enteroids, and methods producing *T. gondii* oocysts in vitro and in vivo in heterologous systems, are provided.

6 Claims, 9 Drawing Sheets

Specification includes a Sequence Listing.

(56) References Cited

OTHER PUBLICATIONS

"International Application Serial No. PCT/US2019/037084, Written Opinion mailed Nov. 14, 2019", 10 pgs.

Pittman, Kelly J., et al., "Z-DNA Binding Protein Mediates Host Control of Toxoplasma gondii Infection", Infection and Immunity, 84(10), (Oct. 2016), 3063-3070.

Powell, Robin H., et al., "WRN conditioned media is sufficient for in vitro propagation of intestinal organoids from large farm and small companion animals", Biology Open, vol. 6, No. 5, (Mar. 27, 2017), XP055620505, (Mar. 27, 2017), 698-705.

Schares, G., et al., "Oocysts of Neospora caninum, Hammondia heydorni, Toxoplasma gondii and Hammondia hammondi in faeces collected from dogs in Germany", International Journal of Parasitology, vol. 35, No. 14, (Dec. 1, 2005), XP027737007, (Dec. 1, 2005), 1525-1537.

Stroud, Chad K., et al., "Disruption of FADS2 gene in mice impairs male reproduction and causes dermal and intestinal ulceration", Journal of Lipid Research, vol. 50, (2009), 1870-1880.

Vaishnava, Shipra, et al., "The Antibacterial Lectin RegIIIg Promotes the Spatial Segregation of Microbiota and Host in the Intestine", Science, 334, (2011), 255-258.

Waap, Helga, et al., "isolation and seroprevalence ofin stray cats and pigeons in Lisbon, Portugal", Veterinary Parasitology, vol. 187, No. 3, (Jan. 17, 2012), XP028492469, (Jan. 17, 2012), 542-547.

"International Application Serial No. PCT US2019 037084, International Preliminary Report on Patentability mailed Dec. 24, 2020", 12 pgs.

Martorelli Di, Genova B., et al., "Intestinal delta-6-desaturase activity determines host range for Toxoplasma sexual reproduction", PLOS Biology, vol. 17, No. 8, E3000364, (Aug. 20, 2019), XP055619380, (Aug. 20, 2019), 1-19.

* cited by examiner a b c

SEQUENCE LISTING

```
<160> NUMBER OF SEQ ID NOS: 11

<210> SEQ ID NO 1
<211> LENGTH: 24
<212> TYPE: DNA
<213> ORGANISM: Artificial Sequence
<220> FEATURE:
<223> OTHER INFORMATION: A synthetic primer

<400> SEQUENCE: 1

gacgacgcct tcaacacctt cttt                                            24


<210> SEQ ID NO 2
<211> LENGTH: 24
<212> TYPE: DNA
<213> ORGANISM: Artificial Sequence
<220> FEATURE:
<223> OTHER INFORMATION: A synthetic primer

<400> SEQUENCE: 2

agttgttcgc agcatcctct ttcc                                            24


<210> SEQ ID NO 3
<211> LENGTH: 20
<212> TYPE: DNA
<213> ORGANISM: Artificial Sequence
<220> FEATURE:
<223> OTHER INFORMATION: A synthetic primer

<400> SEQUENCE: 3

tgcccagcgg gtactacaag                                                 20


<210> SEQ ID NO 4
<211> LENGTH: 20
<212> TYPE: DNA
<213> ORGANISM: Artificial Sequence
<220> FEATURE:
<223> OTHER INFORMATION: A synthetic primer

<400> SEQUENCE: 4

tgccgtgtcg agactagcag                                                 20


<210> SEQ ID NO 5
<211> LENGTH: 20
<212> TYPE: DNA
<213> ORGANISM: Artificial Sequence
<220> FEATURE:
<223> OTHER INFORMATION: A synthetic primer

<400> SEQUENCE: 5

atcaagtcgc acgagacgcc                                                 20


<210> SEQ ID NO 6
<211> LENGTH: 20
<212> TYPE: DNA
<213> ORGANISM: Artificial Sequence
<220> FEATURE:
<223> OTHER INFORMATION: A synthetic primer

<400> SEQUENCE: 6

agcgaattgc gttccctgct                                                 20
```

-continued

```
<210> SEQ ID NO 7
<211> LENGTH: 23
<212> TYPE: DNA
<213> ORGANISM: Artificial Sequence
<220> FEATURE:
<223> OTHER INFORMATION: A synthetic primer

<400> SEQUENCE: 7

gtcttggttc gttgaagggg ctg                                          23


<210> SEQ ID NO 8
<211> LENGTH: 24
<212> TYPE: DNA
<213> ORGANISM: Artificial Sequence
<220> FEATURE:
<223> OTHER INFORMATION: A synthetic primer

<400> SEQUENCE: 8

cgtcctcgat gcccatgaaa tctg                                         24


<210> SEQ ID NO 9
<211> LENGTH: 18
<212> TYPE: DNA
<213> ORGANISM: Artificial Sequence
<220> FEATURE:
<223> OTHER INFORMATION: A synthetic primer

<400> SEQUENCE: 9

ccacgtcctt cgccgatg                                                18


<210> SEQ ID NO 10
<211> LENGTH: 22
<212> TYPE: DNA
<213> ORGANISM: Artificial Sequence
<220> FEATURE:
<223> OTHER INFORMATION: A synthetic primer

<400> SEQUENCE: 10

catcagaggt cccaggttgt cg                                           22


<210> SEQ ID NO 11
<211> LENGTH: 160
<212> TYPE: DNA
<213> ORGANISM: Artificial Sequence
<220> FEATURE:
<223> OTHER INFORMATION: A synthetic promoter

<400> SEQUENCE: 11

caatgtgcac ctgtaggaag ctgtagtcac tgctgattct cgctgttctc ggcaagggct    60

gacgaccgga gtacagtttt tgtgggcaga gccgctgtgc agctttccgt tgttctcggt   120

tgtgtcacat gtgtcattgt cgtgtaaaca cacggttgta                         160
```

*TOXOPLASMA GONDII* VACCINE

CROSS-REFERENCE TO RELATED APPLICATIONS

This application is a U.S. national stage filing under 35 U.S.C. § 371 from International Application No. PCT/US2019/037084, filed on Jun. 13, 2019, and published as WO2019/241579 A1 on Dec. 19, 2019, which claims the benefit of the filing date of U.S. application No. 62/684,524, filed on Jun. 13, 2018, the disclosures of which are incorporated by reference herein.

STATEMENT OF GOVERNMENT RIGHTS

This invention was made with government support under AI123289, AI104697, AI081989 and AI144016 awarded by the National Institutes of Health. The government has certain rights in the invention.

BACKGROUND

Many eukaryotic microbes have complex lifecycles that include both sexual and asexual phases with strict species-specificity. While the asexual cycle of the protistan parasite *Toxoplasma gondii* can occur in any warm-blooded mammal, the sexual cycle is restricted to the feline intestine (Dubey et al., 1970).

*Toxoplasma gondii* is an intracellular parasite which is classified among the Coccidia. This parasite has a relatively broad host range, infecting both mammals and birds. During the asexual cycle, occurring in any warm blooded animal, *T. gondii* exists in two forms: the tachyzoite and the bradyzoite. Tachyzoites, found during acute infection, are the invasive form which is capable of invading all nucleated mammalian cells. After the acute stage of infection, tissue cysts called bradyzoites are formed within host cells and persist within the host organism for the life of the host. Cysts are important in the transmission of infection, especially in humans, as the ingestion of raw or undercooked meat (undercooked pork and lamb are sources in the U.S.) by an individual can result in the ingestion of bradyzoites which can infect the individual resulting in an acute infection. Infection can also occur by eating unwashed vegetables or contaminated water. Oocysts represent the end product of sexual reproduction which occurs only in the intestinal lining of the cat family, from which they are excreted in the feces. Thus, the primary host for *T. gondii* is the cat (wild and domestic), where the parasite is able to sexually reproduce, and the intermediate hosts can include all warm-blooded animals.

It is estimated that 30-50% of the world's population has been exposed to *T. gondii. T. gondii* causes toxoplasmosis, which causes spontaneous abortion in humans and livestock, severe disease in immunocompromised individuals, and may be passed to the fetus during pregnancy. Thus, cats infected with *Toxoplasma* can be a particular risk for pregnant mammals such as humans. However, *T. gondii* may cause few if any symptoms in infected non-cat animals, as it responds to the host immune response by forming dormant tissue cysts (bradyzoites).

Many attempts have been made to develop a vaccine for *T. gondii* infection. A *T. gondii* animal vaccine has been developed for sheep because they so frequently miscarry their fetuses in response to Toxoplasma infection. The vaccine, called Toxovax®, is produced as a tachyzoite and therefore its shelf life is only 10 days. Moreover, after the vial is opened, the contents of Toxovax® must be used within two hours.

SUMMARY

In one embodiment, the disclosure provides a method to produce intestinal organoids (enteroids) from mammalian tissue, for example, fetal cat tissue, and a method to use these organoids to produce *T. gondii* oocysts, which oocysts can be used to provide a *T. gondii* vaccine base, e.g., in a stable, orally infectious form that does not require refrigeration. A Toxoplasma vaccine produced as an oocyst is ideal because it will be stable in any environmental conditions (no refrigeration) for up to two years and it can be an oral inoculation (no needles). Prior to the present disclosure, *T. gondii* was required to be passaged through a cat to regain/maintain its infectivity.

The disclosure thus provides a tissue culture method to produce oocysts from *T. gondii*, oocysts that can be sporulated (i.e., are infective). In one embodiment, the disclosure provides an in vitro method to prepare enteroids. In one embodiment, the method includes mixing one or more portions of a mammalian intestine, such as a fetal feline intestine, e.g., mammalian jejunum having polarized epithelial cells, in a composition comprising a physiologically compatible (aqueous) buffer and a chelator; isolating crypts from the epithelium of the one or more portions of the mammalian intestine, e.g., fetal feline intestine; combining the isolated crypts with a hydrogel and an apoptosis inhibitor, thereby providing a mixture; and culturing the mixture in media so as to result in enteroid formation. In one embodiment, the intestine is jejunum. In one embodiment, the intestine is from the fetus of a domestic cat. In one embodiment, the intestine is from a rodent. In one embodiment, the lumen of the intestine and then the entire intestine are washed and then they are cut into portions prior to agitation. In one embodiment, crypts (e.g., having enterocytes, goblet cells, Paneth cells, endocrine cells and stem cells) and villi (e.g., having enterocytes and goblet cells) are isolated from the epithelium and then crypts are isolated from the villi. In one embodiment, the crypts are isolated using a filter, e.g., about a 50 to 90 micron filter, and resuspended in a matrix, e.g., a hydrogel, and cultured in a medium that promotes enteroid formation. In one embodiment, taurine or an analog thereof, see, e.g., Gupta et al., *Curr. Med Chem.,* 12:2021 (2005) and Chung et al., *Pharmaceuticals,* 5:1128 (2012), the disclosures of which are incorporated by reference herein), analogs including but not limited to hypotaurine, homotaurine, isethionic acid, or cyclic analogs of taurine, or combinations, is/are included in the enteroid medium, e.g., at concentrations ranging from 0.1 to about 25 mM, for instance, about 1 mM to about 10 mM or 4 mM to 6 mM. In one embodiment, the medium for enteroid formation includes one or more of Wnt, Noggin or R-spodin, factors that are present in conditioned media. In one embodiment, one or more apoptosis inhibitors are added to the enteroid medium. In one embodiment, enteroids are isolated from the hydrogel, e.g., 5 or more days after resuspension, and the isolated enteroids are cultured so as to obtain a monolayer of cells. In one embodiment, collagen IV, compositions comprising collagen IV, such as ECL (attachment matrix sold by Millipore having entactin, collagen IV and lamninin) may be included in enteroid medium used to treat the substrate used for monolayer formation. In one embodiment, the isolated enteroids are frozen, e.g., prior to use, in one or more aliquots. The intestinal organoids created by the method that are frozen down, can later be expanded, and are essentially immortal, removing the need to re-isolate crypt cells from the mammal, e.g., fetal cats. In one embodiment, the cells in the monolayer are collected and subjected to conditions that result in a single cell suspension which is then frozen, e.g., in one or more aliquots. In one embodiment, the cells in the monolayer are contacted with *Toxoplasma*, e.g., bradyzoites. In one embodiment, Toxoplasma oocysts are collected from the monolayer. In one embodiment, the collected oocysts are subjected to sporulation to produce infectious oocysts. In one embodiment, the Toxoplasma strain is genetically modified to inhibit tachyzoite formation. In one embodiment, negative selection, e.g., using a negative selectable agent such as fluorodeoxyuridine (FUDR) paired with expression of a marker gene such as uracil phosphoribosyl-transferase (UPT) is employed to obtain oocysts from the infected monolayer. In one embodiment, a negative selectable agent may be employed at concentrations from about 1 μM to about 500 μM, e.g., FUDR may be employed at a concentration from about 10 μM to about 100 μM, about 30 μM to about 60 μM or about 40 μM to about 70 μM. The method may result in release of intracellular oocysts from infected monolayers. In one embodiment, the released oocysts are subjected to sporulation to produce infectious oocysts. The infectious oocysts may be subjected to one or more washes, e.g., with water, a buffer such as normal saline, PBS, HEPES pH 7.4, or any other physiologically compatible buffer, and concentrated, e.g., using centrifugation. The infectious oocysts are then resuspended in water or a physiologically compatible buffer. In one embodiment, oocysts that are obtained in vitro, or in vivo from an organism other than a feline, may have delayed sporulation, delayed by at least 2 to 8 days, 3, 4, 5, 6 or 7 days, delayed infection in a host such as a mouse, e.g., delayed by at least 6 to 21 days, e.g., 7, 10, 14, or 20 days, may not be resistant to 10% bleach, may not be resistant 2% sulfuric acid, or a combination thereof. In one embodiment, oocysts that are obtained in vitro, or in vivo from an organism other than a feline, are resistant to 0.5%, 1%, 2% 3% or 4% bleach. In one embodiment, oocysts that are obtained in vitro, or in vivo from an organism other than a feline, are not resistant to 9%, 8%, 7%, 6% or 5% bleach. In one embodiment, oocysts that are obtained in vitro, or in vivo from an organism other than a feline, are resistant to 1% but not 10% bleach.

The methods described herein to prepare enteroids and monolayers therefrom may thus be employed with crypt cells, e.g., from fetal or adult tissue, from any mammal. For example, adult murine crypt cells were employed to prepare enteroids. In contrast to feline tissue (cats are arachidonic acid auxotrophs), monolayers of murine cells obtained from enteroids may not necessarily need to be cultured with linoleic acid or oxygenated forms thereof, as the addition of an inhibitor of delta 6-desaturase, e.g., SC-26196 in amounts from about 2 μM to 200 μM, to murine organoids in a medium with about 200 μM linoleic acid did not inhibit monolayer formation.

Also provided is a vaccine comprising an effective amount of infectious Toxoplasma oocysts. The vaccine is stable, the shelf life at about 4° C. to about 35° C. is at least 10 days, e.g., greater than 10 days, and up to about 2 years. Moreover, after a vial having the vaccine is opened, the contents may be used for up to at least 1 year. The vaccine may be used to immunize a mammal. In one embodiment, the composition is orally administered. In one embodiment, the composition is parenterally administered. In one embodiment, the composition is administered to the respiratory tract. In one embodiment, the mammal is a human or a non-human primate. In one embodiment, the mammal is a bovine, ovine, swine, canine, feline, equine, or caprine. Since all livestock can be infected with Toxoplasma and when they are, their meat is infectious to humans and other animals, in one embodiment, the mammal to be vaccinated is a bovine, caprine, swine or ovine. In one embodiment, the oocysts in the vaccine are from a strain that is attenuated or avirulent. In one embodiment, the oocysts are genetically modified, e.g., having one, two, three or more genetic modifications. In one embodiment, at least one of the genetic modifications inhibits or prevents cyst formation, e.g., inhibits or prevents cyst wall formation inhibits the cascade that signals cyst formation, inhibits or prevents cyst wall formation, removes an essential cyst metabolic activity, expresses a non-cyst immunodominant epitope, such as SAG1, so that cysts are no longer hidden from the immune response.

Non-feline animals useful to produce *T. gondii* oocysts include but are not limited to mice, rats, ferrets, mink, guinea pig, rabbits and the like. The *T. gondii* oocysts produced by non-feline animals differ in their properties relative to *T. gondii* oocysts produced by felines, e.g., the oocysts produced by the non-feline mammals may be more sensitive to reagents such as bleach and strong acids, e.g., sulfuric acid. The non-feline animals may be administered (treated or exposed to) linoleic acid prior to, during or after exposure, or any combination thereof, to *T. gondii* oocysts. The non-feline animals may be administered (treated or exposed to) one or more inhibitors of delta-6-desaturase, or may be genetically modified so that delta-6-desaturase is not expressed in the animals, e.g., in the gut of the animals, prior to, during or after exposure, or any combination thereof, to *T. gondii* oocysts. In one embodiment, delta-6-desaturase is not expressed in the gut epithelium of the non-feline mammal. In one embodiment, the non-feline animals infected with *T. gondii* oocysts produce at least $10^3$, $10^4$, $10^5$, $10^7$, $10^9$, $10^{10}$ or more oocysts/g feces.

Further provided is a method to immunize (vaccinate) a mammal against *T. gondii* infection, comprising: administering to the mammal an effective amount of isolated infectious *T. gondii* oocysts. As used herein, “isolated” T good/i oocysts have been subjected to at least homogenization and/or filtration, and also optionally subjected to centrifugation including but not limited to sucrose flataion and/or cesium chloride based centrifugation. In one embodiment, a composition for administration further comprises a biologically compatible carrier, e.g., water or saline. In one embodiment, a composition for administration further comprises one or more anti-microbials, such as one or more antibacterial agents. In one embodiment, the mammal is a sheep, goat or swine. In one embodiment, the oocysts are resistant to 1% bleach but not to 10% bleach. In one embodiment, the oocysts are orally administered. In one embodiment, the oocysts are subcutaneously administered. In one embodiment, the oocysts are intraperitonally administered. In one embodiment, a composition comprising the effective amount is administered. In one embodiment, the *T. gondii* oocysts or composition having *T. gondii* oocysts includes both sporulated (infectious) and unsporulated oocysts.

Further provided are knock out non-human mammals, such as knock out rodents. In one embodiment, the disclosure provides for delta-6-desaturase knock out mice. In one embodiment, the delta-6-desaturase knock out mice, such as is described in Stroud et al., *J. Lipid Res.,* 50:1870 (2009) which is incorporated by reference herein, are mated with Z-DNA binding protein, e.g., ZBP1 protein, knock out mice and the progeny thereof are, in one embodiment, more susceptible to oral Toxoplasma infection, e.g., with tachyzoites. The progeny do not need to be exposed to an inhibitor of delta-6-desaturease but will be exposed to linoleic acid in their diet for oocyst production. In one embodiment, wild type mice are mated to Z-DNA binding protein knock out mice and the progeny thereof are, in one embodiment, more susceptible to oral Toxoplasma infection, e.g., with tachyzoites. Knock out non-human mammals may have a genome with a deletion (e.g., an introduced deletion) in the delta-6-desaturase gene, an insertion (e.g., an introduced insertion) in the delta-6-desaturase gene, or a mutation (e.g., an introduced mutation) in the delta-6-desaturase gene, or any combination thereof, for instance, produced by homologous recombination or gene trapping, that results in reduced or the lack of expression of delta-6-desaturase in the non-human mammal. In one embodiment, a Cre/lax system is employed to inactivate, for example, the delta-6-desaturase gene. In one embodiment, a CRISPR system is employed to inactivate, for example, the delta-6-desaturase, gene, optionally in a ZBP knock out background. For instance, mouse embryos may be injected with Cas9 mRNA and at least one single guide RNAs (sgRNA) to generate precise genomic edits in specific loci. Mouse strains with Cre recombinase-dependent Cas9 expression allow for in vivo CRISPR gene editing wherever a vector co-expressing Cre and the sgRNA are introduced. In one embodiment, the knock out non-human mammal may lack of expression of delta-6-desaturase as a result of mating a mouse expressing Cre recombinase linked to a tissue-specific promoter which is optionally inducible, e.g., using an exogenously applied drug such as tetracycline, with a mouse where the delta-6-desaturase gene or a portion thereof is flanked by recombination sites, lox sites. For example, the tissue-specific promoter may be an intestine-specific promoter. In one embodiment, the CRISPR system is employed to add fox-sites flanking the promoter and first exon of the delta-6-desaturase gene, which removes about 1.5 kb of the gene, leaving the rest of the coding region of the gene out of frame. The sites are added to the genome of a mouse with a villin-Cre background where villin is only expressed in the epithelial cells of the intestines, so recombination only occurs in those cells.

In one embodiment, the disclosure provides for a knock out non-human, non feline animal, a mouse, that lacks expression of delta-6-desaturase in at least some cells, wherein the promoter, at least one exon, or both, of the delta-6-desaturase gene is/are deleted in some but not all cells of the knock out. In one embodiment, the animal lacks expression of delta-6-desaturase in intestinal epithelial cells. Also provided is a knock out non-human, non-feline animal that lacks expression of delta-6-desaturase and Z-DNA binding protein. Further provided is a knock out non-human, non-feline animal that lacks expression of delta-6-desaturase, wherein the promoter, at least one exon, or both, of the delta-6-desaturase gene is/are deleted but is/are not replaced by a marker gene.

DETAILED DESCRIPTION

Definitions

Figure 1:
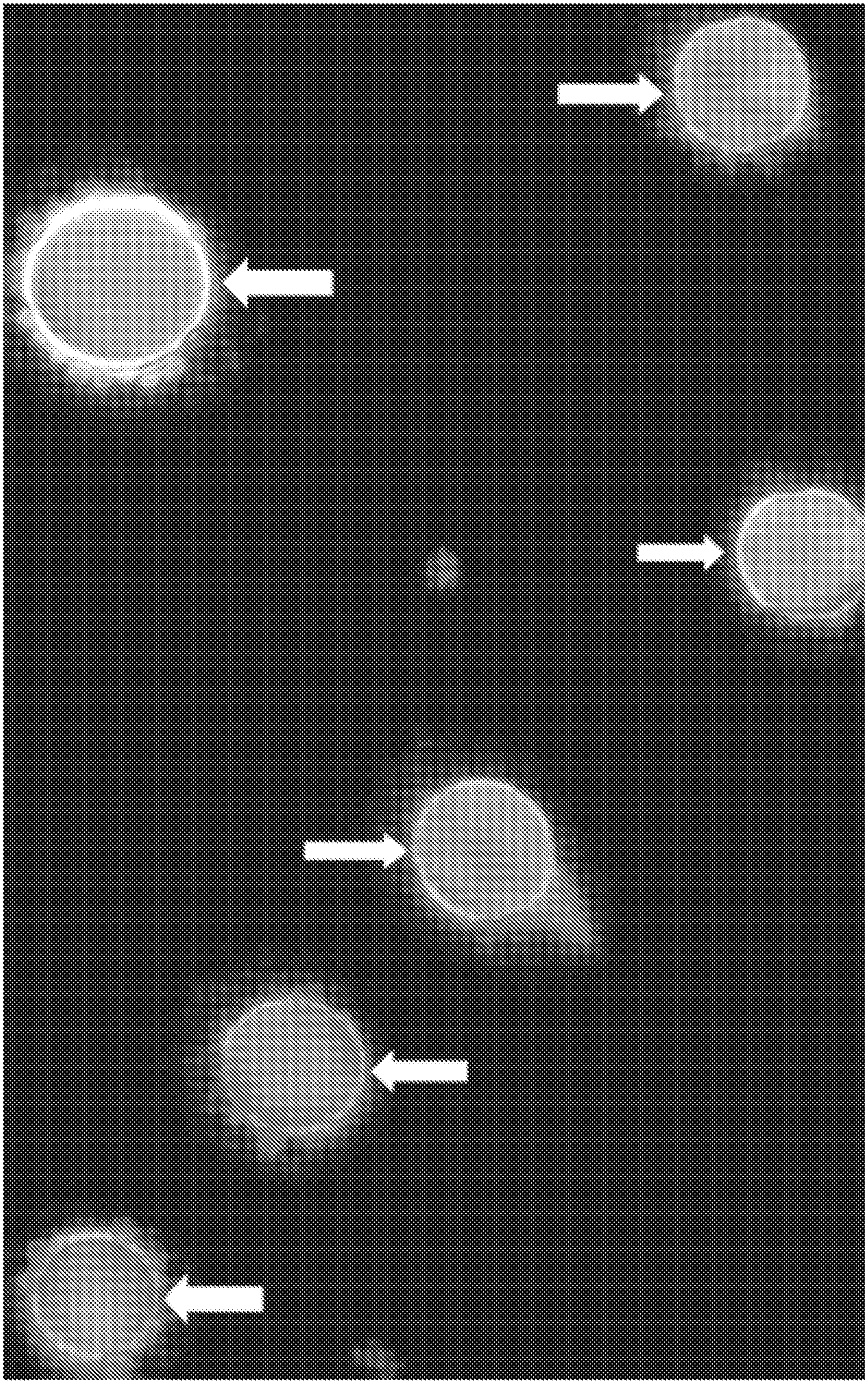
FIG. 1. Oocysts prepared by the method described herein. Arrows point to walls of oocysts.

As used herein, the terms "isolated and/or purified" refer to in vitro preparation, isolation and/or purification of a microbe, e.g., parasite, strain, cell subcellular fraction, nucleic acid, protein, or other molecule or complex, e.g., enteroid, so that it is not associated with and/or is substantially purified from in vitro or in vivo substances. For example, a "recombinant" protein is one expressed using recombinant DNA techniques and a "recombinant" strain or cell is one which has been manipulated in vitro, e.g., using recombinant DNA techniques to introduce changes to the host genome. For example, a "recombinant" strain or cell may be one which has been manipulated in vitro so as to contain an insertion and/or deletion of DNA in the genome, e.g., chromosome, of the strain or cell relative to the genome, e.g., chromosome, of the parent strain or cell from which the recombinant strain or cell was obtained (e.g., "wild-type" strain). In one embodiment, an insertion and/or deletion in the recombinant strain is stable, e.g., the insertion and its corresponding phenotype do not revert to wild-type after numerous passages. Included within the scope of the phrase "recombinant strain" is one which, through homologous recombination, includes a gene which contains a mutation that results in the inactivation of the protein in or reduced expression of the gene, e.g., results in a polypeptide having reduced or lacking biological activity or so that the polypeptide is not expressed, relative to a corresponding wild-type strain that does not include the recombined gene.

The term "operably linked" referred to herein refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

The term "control sequence" referred to herein refers to polynucleotide sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequences. The term "control sequences" is intended to include, at a minimum, all components whose presence is necessary for expression, and can also include additional components whose presence is advantageous, for example, leader sequences and fusion partner sequences.

The term "nucleic acid sequence" or "isolated nucleic acid" means a polymeric form of nucleotides (polynucleotide) of at least about 7 bases in length, either ribonucleotides or deoxynucleotides or a modified form of either type of nucleotide. The term includes single and double stranded forms of DNA. As applied to polynucleotides, the term "substantial identity" means that two polynucleotide sequences, when optimally aligned, share at least 80 percent sequence identity, e.g., at least 90, 92, 93, 94, 95, 96, 97, 98, or 99 percent sequence identity. For example, a SAG1 promoter may have a sequence that has at least 90, 92, 93, 94, 95, 96, 97, 98, or 99 percent sequence identity to the promoter in caatgtgcac ctgtaggaag ctgtagtcac tgctgattct cgctgttctc ggcaagggct gacgaccgga gtacagtttt tgtgggcaga gccgctgtgc agctttccgt tgttctcggt tgtgtcacat gtgtcattgt cgtgtaaaca cacggttgta (SEQ ID NO:11).

As applied to polypeptides, the term "substantial identity" means that two peptide sequences, when optimally aligned, share at least 80 percent sequence identity, e.g., at least 90, 92, 93, 94, 95, 96, 97, 98, or 99, percent sequence identity.

As used herein, an "attenuated" strain means a strain, the inoculation of which to a susceptible mammal, results in reduced (mild) symptoms or manifestations of Toxoplasma infection.

As used herein, an "avirulent" strain means a strain, the inoculation of which to a susceptible mammal, results in no clinical manifestations of Toxoplasma infection.

Exemplary Methods

The apicomplexan parasite *Toxoplasma gondii* causes a chronic infection nearly one third of the human population and is well-known for causing congenital infections leading to blindness, mental retardation, and hydrocephaly of the developing fetus. *T. gondii* has a complex lifecycle containing both sexual and asexual phases. The *T. gondii* asexual cycle can occur in any warm-blooded animal when contaminated food or water is consumed and *T. gondii* disseminates throughout the host, converting to an encysted form in muscle and brain tissue. In contrast, the *T. gondii* sexual cycle is restricted to the feline intestinal epithelium, culminating in the excretion of environmentally resistant oocysts (Dubey et al., 1970).

The sexual cycle of *Toxoplasma gondii* is limited to the feline (cat) intestine where oocysts are formed and subsequently excreted in their feces. Felines useful in obtaining a tissue source, e.g., intestine, to prepare enteroids as described herein are from the family Felidae, including the subfamilies Pantherinae including tigers, lions, jaguars, and leopards, and Felinae including pumas, lynx, ocelot, servals, cheetahs, as well as the domestic and wild cats.

To recapitulate the Toxoplasma sexual cycle in tissue culture, an in vitro protocol was developed to harvest and culture polarized feline intestinal epithelial cells. In one embodiment, Toxoplasma parasites were engineered to express a negative selectable marker from a promoter specific for the asexual stage called tachyzoite. Any strain of *T. gondii* may be engineered. Exemplary negative selectable agents include but are not limited to 5'-fluoro-2'-deoxyuridine (FUDR). Tachyzoite specific promoters include but are not limited to SAG1, SAG2A, SAG3, SRS1, SRS2, or SRS3 promoters. The vector encoding the negative selectable marker gene may be inserted into the *T. gondii* genome, e.g., via homologous recombination resulting in an insertion or deletion of part of the host genome, or randomly inserted into the genome. Addition of the negative selection agent inhibits the rapidly replicating asexual tachyzoites from lysing the intestinal cells, which gives the sexual stage (oocysts) time to develop. The oocysts may be employed in a vaccine because Toxoplasma oocysts are stable in any environmental conditions for up to 2 years and they are orally infective. In one embodiment, the *T. gondii* strain employed in the methods is not genetically engineered and/or selection is not employed.

Methods to Prepare Enteroids, Prepare Monolayers from Enteroids and Obtain Oocysts Thus, the disclosure provides an in vitro method to prepare mammalian enteroids. The method includes agitating one or more portions of mammalian jejunum obtained from a mammal, e.g., one that is not an arachidonic acid auxotroph, in a composition comprising a physiologically compatible buffer and a chelator; isolating crypts from epithelium of the one or more agitated portions of the jejunum; combining the isolated crypts, a hydrogel and optionally an apoptosis inhibitor, thereby providing a mixture; and culturing the mixture in medium so as to result in enteroid formation. In one embodiment, the mammal is an adult. In one embodiment, the mammal is a fetus. In one embodiment, the mammal is a newborn. In one embodiment, the mammal is a juvenile. In one embodiment, the mammal is a mouse. In one embodiment, the medium comprises at least one TGF-beta inhibitor. In one embodiment, the medium comprises at least one apoptosis inhibitor. In one embodiment, the medium comprises taurine or an analog thereof. In one embodiment, the medium comprises at least one TGF-beta inhibitor, at least one apoptosis inhibitor and optionally taurine or an analog thereof.

In one embodiment, fetal intestinal tissue, e.g., from the third trimester which in domestic cats is about days 38-60 of gestation, is obtained from a pregnant feline within an hour or so from extraction, e.g., within 10-20 minutes of interruption of blood circulation via the uterus if at room temperature but longer if colder conditions or icing of the uterus is employed. In one embodiment, fetal intestinal tissue including the duodenum is isolated. In one embodiment, the intestinal tissue includes duodenal tissue beginning about 0.5 cm to about 2 cm, e.g., about 1 cm, from the stomach until about 5 to about 15 cm, about 10 cm, from the cecum. The intestinal tissue is placed into a cold buffer, e.g., a physiologically compatible buffer such as PBS, normal saline (0.9% NaCl) or bicarbonate buffer, and the lumen of the intestine is washed, for instance, repeatedly, with the cold buffer. In one embodiment, the epithelial layer is exposed and optionally cut into smaller sections.

To isolate crypt cells, the exposed layer or sections are washed in a buffer such as a physiologically compatible buffer that optionally has one or more antibiotics, e.g., using a rotator, for about 5 to 20 minutes, then rinsed with a fresh aliquot of the buffer that optionally has one or more antibiotics, before placing the layer or sections in a buffer having one or more chelators, EDTA, IDA, or DTPA, and optionally one or more antibiotics, at about 4° C. for about 20-40 minutes with agitation. After incubation, the epithelial cells are collected by scraping the layer or section(s). Crypts cells are separated from villi, e.g., by centrifugation and/or filtration, then crypt cells are resuspended in a hydrogel, e.g., one containing laminin, collagen IV, heparin sulfate proteoglycan, entactin/nidogen, or any combination thereof, which hydrogel optionally contains one or more growth factors (or the growth factors may be added with the crypt cells), then aliquoted, for example, into wells of a tissue culture plate. Enteroid medium and an apoptosis inhibitor are added to each well.

Apoptosis inhibitors useful in the methods include but are not limited to one or more of Rock inhibitor Y27632, GSK-3 inhibitor CHIR99021, 10058-F4, 4'-methoxyflavone, Z-VAD-FMK, Z-VAD(OMe)-FMK, Decylubiquinone, Sodium Orthovanadate, Calyculin A, PMA, Cyclosporin A, Necrostatin-1, Caffeine, Autophagy inhibitor, 3-MA, MnTBAP chloride, Salubrinal, Calpeptin, Caspase-3 Inhibitor, KT5823, bpV(pic), Calphostin C, Caspase-8 inhibitor II, Bongkrekic acid, ABT 263, ALLN, Sodium phenylbutyrate, 2-Deoxy-D-glucose, Trolox, SIRT1 Activator 3, Melatonin, Hemin chloride, Caspase-1 inhibitor VI, Muscone, MDL-28170, Z-DEVD-FMK, Caspase-1 inhibitor I, Hypericin, Thiorphan (DL), Caspase-1 Inhibitor II, Q-VD-OPH, Z-VD-VAD-FMK, Dexamethasone, Aurintricarboxylic Acid, Maprotiline Hydrochloride, Oxaliplatin, Carvedilol, Heptelidic acid, JNK Inhibitor VIII, Mdivi-1, HBED, 4-Amino-1,8-naphthalimide, LY 364947, Gambogic amide, Ivachtin, Colivelin, 3-Aminobenzamide, Ro 08-2750, 7,8-Dihydroxyflavone, Omi/HtrA2 Protease Inhibitor, Ucf-101, BI-6C9, Orsellinic acid, Guanosine 3prime5prime-cyclic Monophosphate, Sodium Salt, 5-AIQ hydrochloride, 8-Chloro-dibenz [b,f][1,4]oxazepine-10(11H)-carboxylic acid 2-[1-oxo-3-(4-pyridinyl)propyl]hydrazide monohydrochloride, Pidotimod, Boc-L-aspartic acid beta-benzyl ester chloromethylketone, Bax channel blocker, Bax channel blocker, PD 151746, PARP Inhibitor XII, Carbachol, MCI-186, Sodium Pyruvate, Danmacanthal, p38 MAP Kinase Inhibitor IV, Razoxane, Myeloperoxidase Inhibitor-I, Cesium Chloride, R(−)-Deprenyl hydrochloride, Amifostine, Bilobalide, Apoptosis Inhibitor, alpha-Tocotrienol, Cyclosporin A-d4, Necrostatin-1 inactive control, Cinnamtannin B-1, Ipsapirone, Tyrphostin AG 99, 3-ATA, PAPA NONOate, Z-Asp-2,6-dichlorohenzoyloxymethylketone, Okadaic Acid, Ammonium Salt, Rasagiline Mesylate, 7,8-dichloro-1,4-dihydro-4-oxo-3-quinolinecarboxylic acid, TGF-beta RI Kinase Inhibitor III, Cdk2 substrate, NS3694, BEPP monohydrochloride, GW-441756, CAY10500, Bongkrekic Acid, Triammonium Salt, CAY10578, Fructose-proline, Linomide, BTZO 1, (+/−)-Huperzine A, 7-nitro-10-octyl-3-phenyl-pyrimido[4,5-b]quinoline-2,4(3H,10H)-dione, Hexarelin, Suptopin-2, iMAC2, R5C3, BBMP, U 82836E, AG 490, m-CF3, Maslinic Acid, Me-7BIO, thio-Miltefosine, Ginkgolide J, Terameprocol, Sodium Ursodeoxycholate, Didox, Pyruvic acid, Taurodeoxychloic acid, Pentachloropyridine, Biotin-VAD-FMK, NAP, Glycidyl Palmitate, Z-WEHD-FMK, Z-AEVD-FMK, NSC348884, DL-alpha-Difluoromethylornithine hydrochloride, GW1929, or Ferrostatin 1.

In one embodiment, an apoptosis inhibitor useful in the methods includes but is not limited to one or more of AZD5438, BAG1 (72-end), GST tagged human recombinant, expressed in *E. coli*, BAX Inhibiting Peptide V5, BEPP monohydrochloride, BI-6C9, BTZO-1, Bongkrekic acid solution from *Pseudomonas cocovenenans*, CTP Inhibitor, CTX1, Calpeptin, Clofarabine, Clusterin (nuclear form), Clusterin (secretory form), Combretastatin A4, Cyclic Pifithrin-α, EM20-25, Fasentin, Ferrostatin-1, GNF-2, IM-54, Ischemin, Liproxstatin-1, MDL 28170, Mdivi-1, Mitochondrial Fusion Promoter M1, N-Ethylmaleimide, N-Ethylmaleimide, NS3694, NSCI, Necrostatin-1, Oridonin, PD 151746, PDI inhibitor 16F16, Pentostatin, Pifithrin-α, Pifithrin-μ. Pifithrin-α, p-Nitro, Cyclic—CAS 60477-38-5, Pifithrin-μ, CAS 64984-31-2, Piperlongumine, R18 trifluoroacetate, S-15176, UCF-101, p53-Snail binding inhibitor, or GN25.

Enteroid media may contain one or more of conditioned media, as well as media such as DMEM, MEM, and/or RPMI, L-glutamine or an analog thereof, e.g., glutamax, HEPES or other buffer, and optionally supplements including one or more of N2, B27, N-acetylcysteine, nicotinamide, insulin, selenium, transferrin, and optionally growth factors, e.g., EGF, insulin, FBS, or one or more MATRIGEL components.

The media and the inhibitor may be replaced every day, e.g., for up to three days. Enteroids are obtained within 2 to 5 days.

The hydrogel containing enteroids is collected and then subjected to a shear force, e.g., by passage through a needle. The enteroids are separated from the hydrogel, e.g., using filtration or centrifugation, to isolate the cells. The cells, a single cell suspension, are rinsed with a buffer, resuspended in enteroid medium, then plated onto a surface, e.g., one coated with ECL (Millipore) or proteins including but not limited to entactin, collagen IV, laminin, or combinations thereof. Confluent monolayers form within about one to two weeks. The cells may be frozen down, e.g., after removal from the plate, centrifugation for 5 min at 80×g, washing at least one or twice in a buffer such as PBS, then frozen in growth media with a cryopreservative, e.g., 5% DMSO. Prior to infection, monolayers are incubated with a polyunsaturated fatty acid, e.g., a C10-C20 carbon chain with two, three or four double bonds, or oxygenated forms thereof, e.g., oxygenated forms of linoleic acid and optionally albumin, e.g., BSA or HSA, polyvinyl alcohol, or Prionex®.

Bradyzoites, e.g., from a *T. gondii* strain with a negative selectable marker expressed from a tachyzoite specific promoter, are used to infect the monolayers and oocysts are collected thereafter. Oocyst viability can be tested using sporulation assays.

As also disclosed herein, the mechanism of species specificity for *T. gondii* sexual development is disclosed and the species barrier broken to allow the sexual cycle to occur in a non-feline, mice. It was determined that *T. gondii* sexual development occurs when cultured feline intestinal epithelial cells are supplemented with linoleic acid. Felines are the only mammals that lack delta-6-desaturase activity in their intestines, which is required for linoleic acid metabolism, resulting in systemic excess of linoleic acid (Rivers et al., 1975; Sinclair et al., 1979). It was found that inhibition of murine delta-6-desaturase and supplementation of their diet with linoleic acid allowed *T. gondii* sexual development in mice. This mechanism of species specificity is the first defined for a parasite sexual cycle. This highlights how host diet and metabolism shape coevolution with microbes. The key to unlocking the species boundaries for other eukaryotic microbes may also rely on the lipid composition of their environments as there is increasing evidence for the importance of host lipid metabolism during parasitic lifecycles (Toledo et al., 2016; Lujan et al., 1996), Pregnant women are advised against handling cat litter as maternal infection with *T. gondii* can be transmitted to the fetus with potentially lethal outcomes. Knowing the molecular components that create a conducive environment for *T. gondii* sexual reproduction will allow for development of therapeutics that prevent shedding of *T. gondii* parasites. Finally, this work will allow the *T. gondii* field to use of alternative models.

Vaccines

The vaccines of the present disclosure that include Toxoplasma oocysts may further comprise one or more suitable pharmaceutically acceptable carriers. As used herein, the term "pharmaceutically acceptable carrier" refers to an acceptable vehicle for administering a vaccine to mammals comprising one or more non-toxic excipients which do not react with or reduce the effectiveness of the pharmacologically active agents contained therein. The proportion and type of pharmaceutically acceptable carrier in the vaccine may vary, depending on the chosen route of administration. Suitable pharmaceutically acceptable carriers for the vaccines of the present disclosure are described in the standard pharmaceutical texts. See, e.g., "Remington's Pharmaceutical Sciences", $18^{th}$ Ed., Mack Publishing Company, Easton, Pa. (1990). Specific non-limiting examples of suitable pharmaceutically acceptable carriers include water, saline (e.g., PBS), dextrose, glycerol, ethanol, or the like and combinations thereof. In one embodiment, the composition may also comprise a bile acid or a derivative thereof, in particular in the form of a salt. These include derivatives of cholic acid and salts thereof, in particular sodium salts of cholic acid or cholic acid derivatives. Examples of bile acids and derivatives thereof include cholic acid, deoxycholic acid, chenodeoxycholic acid, lithocholic acid, ursodeoxycholic acid, hydroxycholic acid and derivatives such as glyco-, tauro-, amidopropyl-1-propanesulfonic-, amidopropyl-2-hydroxy-1-propanesulfonic derivatives of the aforementioned bile acids, or N,N-bis (3 Dgluconoamidopropyl) deoxycholamide. A particular example is sodium deoxycholate (NaDOC).

In addition, if desired, the vaccine can further contain minor amounts of auxiliary substances such as agents that enhance the effectiveness of the composition, stabilizers, preservatives, and the like.

Examples of suitable stabilizers include protease inhibitors, sugars such as sucrose and glycerol, encapsulating polymers, chelating agents such as ethylene-diaminetetracetic acid (EDTA), proteins and polypeptides such as gelatin and polyglycine and combinations thereof.

Optionally, the composition may further comprise an adjuvant. Suitable adjuvants for inclusion in the compositions of the present disclosure include those that are well known in the art, such as complete Freund's adjuvant (CFA) that is not used in humans, incomplete Freund's adjuvant (IFA), squalene, squalene, alum, and various oils, all of which are well known in the art, and are available commercially from several sources, such as Novartis Novartis' MF59 adjuvant).

Depending on the route of administration, the vaccine may take the form of a solution, suspension, emulsion, or the like. A vaccine of the present disclosure can be administered orally or through parenteral administration, such as through sub-cutaneous injection, intra-muscular injection, intravenous injection, intraperitoneal injection, or intra-dermal injection to a mammal, e.g., humans, domestic cats or livestock. Typically, the vaccine is orally administered.

For parenteral administration, the vaccines of the present disclosure may be administered by intravenous, subcutaneous, intramuscular, intraperitoneal, or intradermal injection, which optionally may further comprise pharmaceutically accepted carriers. For administration by injection, the vaccine may be a solution in a sterile aqueous vehicle which may also contain other solutes such as buffers or preservatives as well as sufficient quantities of pharmaceutically acceptable salts or of glucose to make the solution isotonic.

The vaccine may be delivered locally to the respiratory system, for example to the nose, sinus cavities, sinus membranes or lungs, in any suitable manner, such as by inhalation via the mouth or intranasally. The vaccines can be dispensed as a powdered or liquid nasal spray, suspension, nose drops, a get or ointment, through a tube or catheter, by syringe, by packtail, by pledget, or by submucosal infusion. The vaccines may be conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the vaccine and a suitable powder base such as lactose or starch. Examples of intranasal formulations and methods of administration can be found in PCT publications WO 01/41782, WO 00/33813, and U.S. Pat. Nos. 6,180,603; 6,313,093; and 5,624,898, all of which are incorporated herein by reference and for all purposes. A propellant for an aerosol formulation may include compressed air, nitrogen, carbon dioxide, or a hydrocarbon based low boiling solvent. The vaccines of the present disclosure can be conveniently delivered in the form of an aerosol spray presentation from a nebulizer or the like. In some aspects, the active ingredients are suitably micronized so as to permit inhalation of substantially all of the active ingredients into the lungs upon administration of the dry powder formulation, thus the active ingredients will have a particle size of less than 100 microns, desirably less than 20 microns, and preferably in the range 1 to 10 microns. In one embodiment, the vaccine is packaged into a device that can deliver a predetermined, and generally effective, amount of the vaccine via inhalation, for example a nasal spray or inhaler.

The vaccines of the present disclosure are administered prophylactically. For instance, administration of the vaccine may be commenced before or at the time of infection. In particular, the vaccines may be administered up to about 1 month or more, or more particularly up to about 4 months or more before the mammal is exposed to *T. gondii*. Optionally, the vaccines may be administered as soon as 1 week before infection, or 1 to 5 days before infection.

The desired vaccine dose may be presented in a single dose or as divided doses administered at appropriate intervals, for example as two, three, four or more sub-doses per day. Optionally, a dose of vaccine may be administered on one day, followed by one or more booster doses spaced as desired thereinafter. In one exemplary embodiment, an initial vaccination is given, followed by a boost of the same vaccine approximately one week to 15 days later.

The compositions may be formulated with conventional carriers and excipients, which will be selected in accord with ordinary practice. Aqueous formulations are prepared in sterile form, and when intended for delivery by other than oral administration, are generally be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone they may be present as pharmaceutical formulations. The formulations, both for veterinary and for human use, comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, PA). Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

Pharmaceutical formulations according to the present invention may include one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight), The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for intrapulmonary or nasal administration may have a particle size for example in the range of 0.1 to 500 microns (including particle sizes in a range between 0.1 and 500 microns in increments of microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of a given condition.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use, Extemporaneous injection solutions and suspensions are prepared from sterile powders, granules and tablets of the kind previously described. Exemplary unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Specific dosages may be adjusted depending on conditions of the age, body weight, general health conditions, sex, diet, lifestyle and/or current therapeutic regimen of the mammal, as well as for intended dose intervals, administration routes, excretion rate, and combinations of drugs. An effective dose may depend at least on whether the active ingredient is being used prophylactically (e.g., lower doses may be employed), the method of delivery, and the pharmaceutical formulation, and will be determined by the clinician using conventional dose escalation studies. Any of the dosage forms described herein containing effective amounts are well within the bounds of routine experimentation and therefore, well within the scope of the instant disclosure.

In one embodiment, a vaccine dose may include from about 10 to about 100,000 oocysts, about 50 to about 50,000 oocysts, about 100 to about 10,000 oocysts, about 10,000 to about 30,000 oocysts, about 50 to about 1,000 oocysts, about 1,000 to about 5,000 oocysts, or about 5,000 to about 10,000 oocysts.

The desired dose of the composition may be presented in a continuous infusion, a single dose, or as divided doses administered at appropriate intervals, for example as two, three, four or more sub-doses per day. Optionally, a dose of composition may be administered on one day, followed by one or more booster doses spaced as desired thereinafter. In one exemplary embodiment, an initial dose is given, followed by a boost of the same composition approximately two to four days later. In one particular embodiment, the mammal is administered a first dose of the composition at about 48 hours post-infection and a second dose of the composition at about 96 hours post-infection. Other dosage schedules may also be used, e.g., prophylactic use during an outbreak or pandemic to decrease morbidity post infection.

Following an initial administration of the composition, mammals may receive one or several booster doses adequately spaced thereafter. In some embodiments, the booster doses comprise the same amounts and type of active agent as the initial administration. In other embodiments, the booster doses may comprise a reduced amount and/or a different type of active agent.

EXEMPLARY EMBODIMENTS

In one embodiment, the disclosure provides an in vitro method to prepare mammalian enteroids. The method includes agitating one or more portions of mammalian jejunum in a composition comprising a physiologically compatible buffer and a chelator; isolating crypts from epithelium of the one or more agitated portions of mammalian jejunum; combining the isolated crypts, a hydrogel and an apoptosis inhibitor, thereby providing a mixture; and d) culturing the mixture in medium so as to result in enteroid formation. In one embodiment, the mammal is a feline. In one embodiment, the jejunum is from the fetus of a feline. In one embodiment, the method further includes washing the lumen of the jejunum and/or washing the jejunum prior to agitating the one or more portions. In one embodiment, crypts and villi are isolated from the epithelium and then crypts are isolated from the villi. In one embodiment, the crypts are isolated from the villi using a filter. In one embodiment, the method further includes isolating enteroids from the hydrogel and culturing the isolated enteroids so as to obtain a monolayer of cells. In one embodiment, the method also includes collecting the cells in the monolayer. In one embodiment, the method further includes freezing one or more aliquots of the collected cells. In one embodiment, the method also includes removing the supernatant from the cells in the monolayer and adding medium and Toxoplasma bradyzoites to the cells. In one embodiment, the cells are cultured under conditions that inhibit tachyzoite formation by the bradyzoites. In one embodiment, the method also includes isolating Toxoplasma oocysts from the cells. In one embodiment, the Toxoplasma is genetically modified to inhibit tachyzoite formation, e.g., the genetic modification comprises an expression cassette comprising a negative selectable marker. In one embodiment, the genetic modification comprises an expression cassette comprising a tachyzoite specific promoter. In one embodiment, the method includes inducing sporulation of the isolated Toxoplasma oocysts, thereby producing infectious Toxoplasma oocysts. In one embodiment, the method includes isolating enteroids and freezing one or more aliquots of the enteroids. In one embodiment, the mixture further comprises a TGF-beta inhibitor. In one embodiment, the mixture comprises taurine or an analog thereof. In one embodiment, the mixture comprises a TGF-beta inhibitor and taurine or an analog thereof.

Also provided is an in vitro method to prepare Toxoplasma oocysts. The method includes infecting mammalian jejunum derived cells, from an organoid, with Toxoplasma bradyzoites; and isolating Toxoplasma oocysts. In one embodiment, the method further includes sporulating the isolated Toxoplasma oocysts to produce infectious Toxoplasma oocysts. In one embodiment, the mammal is a feline, mouse, rat, guinea pig, or rabbit. In one embodiment, the cells are fetal feline jejunum derived cells. In one embodiment, the cells are rodent jejunum derived cells. In one embodiment, non-feline cells are exposed to a delta-6-saturase inhibitor, e.g., before, during after, infection, or any combination thereof. In one embodiment, the cells are exposed to linoleic acid, e.g., before, during or after infection, or any combination thereof. In one embodiment, the bradyzoites comprise a genetic modification that inhibits tachyzoite formation. In one embodiment, the genetic modification comprises an expression cassette comprising a negative selectable marker. In one embodiment, the genetic modification comprises an expression cassette comprising a tachyzoite specific promoter. In one embodiment, a negative selection agent is not employed during infection.

In one embodiment, an in vivo method to prepare *T. gondii* oocysts in a non-feline mammal is provided. The method includes contacting a non-feline mammal with *T. gondii* bradyzoites and an effective amount of an inhibitor of delta-6-desaturase; and collecting feces of the non-feline mammal having the oocysts. In one embodiment, the mammal is not a primate. In one embodiment, the mammal is not a ruminant. In one embodiment, the inhibitor of delta-6-desaturase comprises SC26196, norflurazone, RNAi, or CP 24879 (p-isopentoxyaniline). In one embodiment, the mammal is a mouse, rat, ferret, mink, rabbit, beaver, mongoose, or guinea pig. In one embodiment, the method further includes isolating *T. gondii* oocysts, e.g., by collecting feces having the oocysts. In one embodiment, the method also includes subjecting the material having the oocysts to filtration and one or more separation involving centrifugation. In one embodiment, the *T. gondii* oocysts are more sensitive to bleach or sulfuric acid than *T. gondii* oocysts produced by cats. Isolated *T. gondii* oocysts resistant to 1% bleach but not to 10% bleach or 2% sulfuric acid are also provided, as well as a pharmaceutical composition comprising an amount of the isolated *T. gondii* oocysts, e.g., effective to immunize a mammal.

Further provided is an in vivo method to prepare *T. gondii* oocysts in a non-feline mammal. The method includes contacting a non-feline mammal that does not express or has reduced expression of delta-6-desaturase with *T. gondii* bradyzoites; and collecting feces of the non-feline mammal having the oocysts. In one embodiment, the mammal is not a primate or a ruminant. In one embodiment, the mammal is a mouse, rat, ferret, mink, rabbit, beaver, or guinea pig. In one embodiment, the non-feline mammal is genetically modified to not express delta-6-desaturase, e.g., in the gut of the mammal. In one embodiment, the method further includes isolating *T. gondii* oocysts. In one embodiment, the *T. gondii* oocysts produced in a non-feline mammal are more sensitive to bleach or strong acids, e.g., sulfuric acid, than *T. gondii* oocysts produced by cats. In one embodiment, a non-human, non-feline mammal having a knock-out of delta-6-desaturase is employed to prepare oocysts.

In one embodiment, a method to purify *T. gondii* oocysts is provided. The method includes, in one embodiment, homogenizing fecal material from a mammal that has *T. gondii* oocysts; filtering the homogenate to obtain a filtrate having the oocysts; separating the filtrate via centrifugation into a supernatant and a pellet having the oocysts; resuspending the pellet; subjecting resuspended pellet to sucrose centrifugation into a supernatant having the oocysts and a pellet; collecting the supernatant from the sucrose centrifugation and subjecting the supernatant centrifugation into a supernatant and a pellet having the oocysts; g) resuspending the pellet in a salt solution and subjecting the resuspended pellet to cesiu chloride centrifugation into a supernatant and a pellet having the oocysts; and collecting the pellet.

The invention will be described by the following non-limiting examples.

Example 1

The asexual cycle of the parasite *Toxoplasma gondii* occurs in any warm-blooded animal, but the sexual cycle is restricted to the feline intestine. Creating cell culture conditions for *T. gondii* sexual development allows for classical genetic crosses and for a molecular analysis of the sexual stages. Herein is described an in vitro method for the production of infectious oocysts, the final stage of sexual development, from feline intestinal organoids. For sexual development to occur in cell culture, growth of the rapidly replicating asexual form, called a tachyzoite, needs to be inhibited. *T. gondii* parasites were engineered to express a negative selectable marker from a tachyzoite-specific promoter.

When the tissue cyst forms, called a bradyzoite, it invades the feline intestinal epithelium, either differentiating into the rapidly replicating form called a tachyzoite to begin the asexual cycle or developing into type A schizonts that initiate the sexual cycle. In previous attempts at cell culture sexual development of *T. gondii*, tachyzoites lysed the monolayer before the sexual stages formed. To inhibit the growth of asexual tachyzoites, a negative selectable marker, uracil phosphoribosyl-transferase (UPT), was linked to a tachyzoite specific promoter, e.g., Surface Antigen 1 (SAG1). This ΔUPT::SAG1-UPT strain phosphoribosylates the uracil analog 5-fluorodeoxyuridine (FUDR) only during the tachyzoite stage. The UPT gene in *T. gondii* was deleted, then reintroduced under the control of SAG1.

Methods

Modified Toxoplasma strains: As *T. gondii* loses its ability to undergo sexual development after it has been passaged too long in tissue culture, the sexual competence of each strain is maintained after each genetic manipulation. To generate ΔUPT::SAG1-UPT, first the UPT gene was deleted in the *T. gondii* ME49 strain using the previously published UPT deletion construct (Donald et al., 1995) and selection with 5-50 μM FUDR. To generate SAG1-UPT, UPT was PCR amplified from *T. gondii* cDNA with a Nsi I site to the 5'end and a Nde I site on the 3'end, then subcloned into Nsi I and Nde I digested SAG1-βgal (Seeber et al., 1996).

Dissection of Kitten Fetus

1. Open uterus right after the surgery and remove fetus.
2. Make a cut in the abdomen and expose the organs, specifically the intestine.
3. Recognize the small intestine by locating the stomach and the cecum (portion of intestine between the small and large intestine).
4. Pull out the stomach and expose the beginning of the small intestine (duodenum). Cut 1 cm after the stomach and with a tweezers pull out the intestine until the cecum is located. Best enteroid yields are observed using jejunum.
5. Cut 10 cm before the cecum.
6. Let the small intestine sit in cold PBS.

7. Wash intestinal lumen by injecting cold PBS into one end. Repeat until the intestine is cleaner (2-3 times)
8. Open up intestinal section and expose epithelial layer.
9. Cut the intestine into smaller, e.g., about 1 cm, sections.

Crypt Isolation

1. Wash intestinal sections by letting them rotate in PBS+antibiotic penicillin/streptomycin) for 10 minutes in cold room, e.g., at about 4° C.
2. Rinse the intestinal tissues with 5 mL of fresh PBS+ antibiotic. Remove the supernatant and resuspend the tissue in 5 mM EDTA in PBS+antibiotics. Incubate 30 minutes at 4° C. with agitation.
3. Remove the supernatant and with a tweezers pick up one intestinal segment. By the microscope visualize the side that contains the epithelial tissue. Scrape the epithelial tissue using a razorblade in order to remove the crypts and
4. Filter using 70 μm cell strainer to remove villi but keep the crypts. Some villi will remain
5. Collect about 200 crypts per sample.

Plating the Cells

1. Spin crypts at 250×g for 10 minutes at 4° C. and decant supernatant.
2. Resuspend crypts in MATRIGEL—about 1 crypt/μL. Mix up and down a couple of times.
3. Add 50 μl of MATRIGEL-cell suspension per well into 24 well plates (right at the center). Pipet up and down after adding suspension to each well to get even mixture.
4. Let it sit for at least 10 minutes to solidify.
5. Add 500 μl of medium+an apoptosis inhibitor, e.g., a ROCK inhibitor such as Y27632 may be included at about 5 to about 20 μM, a TGF-beta inhibitor such as CHIR99021 may be used at about 0.5 to about 4 μM, e.g., Y27632 may be employed at 10 μM and CHIR99021 may be employed at 2.5 μM. Taurine or an analog thereof may also be included in the medium.
6. Change media every day the first 3 days. After day 3 Y compound is not needed,
7. Enteroids should be visible after day 2 to day 5.

Exemplary Enteroid Medium Recipe

Conditioned media is made by incubating L-WNR cells (ATCC® CRL-3276) with DMEM-F12 20% FBS for 4 days.

TABLE 1

Exemplary Enteroid Medium

| Component | (50 mL total) | Final concentration in comp media |
|---|---|---|
| Conditioned medium | 25 mL | — |
| Advanced DMEM/F12 | 20 mL | NA |
| Glutamax (100X-200 mM) | 250 uL | 1X |
| HEPES(100X, 1M) | 1000 uL | 1X |
| N2 supplement (100X) | 500 uL | 1X |
| B27 (50x) | 1 mL | 1X |
| Pen/Strep (100X) | 500 uL | ~1X |
| N-acetylcysteine (500 mM) | 100 uL | 1 mM |
| Nicotinamide (1M) | 500 uL | 10 mM |
| Insulin/selenium/transferrin (100X) | 500 uL | 1X |
| EGF 50 ug/mL** | 50 uL | 50 ng/mL |

**Add EGF when ready to combine; degrades in about 1 week.

Monolayer Preparation

1. Incubate coverslip or Snapwell™ or other transwell permeable support with a membrane, e.g., a 0.4 μm pore polycarbonate membrane, supported by a detachable ring, in a solution of Entactin-Collagen Laminin (catalog number 08-110, Millipore) diluted 5× in PBS (10 uL of ECL in 40 uL Media)
2. Next day: Remove enteroid media using 1 mL, tip.
3. Using 500 uL of ice-cold PBS, pipette, resuspend and collect the MATRIGEL from the plate well.
4. Using a 25.8-G needle, shear the enteroids and break them open to release dead cell buildup in the lumen. Pass enteroids through needle by sucking them up through the needle and expelling them back through one time into a micro centrifuge tube.
5. Spin at 200×g @ 4 degree for 5 minutes. Layers of MATRIGEL and enteroids will form.
6. Remove all supernatant and MATRIGEL layer (MATRIGEL layer is crystal clear and it's right above the cell pellet)
7. Rinse the cells with ice cold PBS.
8. In case enteroids are overgrown they can be treated with 0.25 trypsin solution for few minutes in order to get a single cell solution, which enhances adherence of the cells.
9. Resuspend cells in fresh Enteroid medium and add them into the snapwells or coverslips.
10, Cells attach within one hour and forma full confluent monolayer in 7-14 days.
11. Incubate monolayers with about 50 to 200 μM Linoleic Acid-BSA complex 24 hours before infection. The Linoleic-BSA complex is made by adding 2 μL of Linoleic acid, 4 μL NaOH in 996 μL of 7.5% BSA in PBS 1×. The complex is incubated for one hour at 37° C. and the final Linoleic acid-BSA concentration is 6 mM.

Bradyzoite Extraction and Enteroid Infection

1. Dissect Mice 21-28 days after infection with oocyst and extract the brains. Homogenize the tissue using a pestle and 10 mL of cold Tween 80 1% in PBS.
2. Spin at 400×g @ 4° C. for 10 minutes and discard the supernatant. Resuspend the pellet in Dextran 20% solution in DMEM F12.
3. Spin at 2200×g 4° C. for 10 minutes. Remove carefully the initial layer containing brain tissue. Brain cysts are in the pellet (white pellet).
4. Resuspend brain cysts in 1 mL of Pepsin solution (0.01% pepsin) at room temperature for 1 minute with agitation. After 1 minute add 1 mL of sodium carbonate and 1 mL of fresh enteroid medium.
5. Spin at 250×g @ 4° C. for 10 minutes. The bradyzoites are in the pellet.
6. Resuspend tissue Bradyzoites in Enteroid medium plus Y compound (1:1000 apoptosis inhibitor).
7. Usually 1 Brain has Bradyzoites enough to infect 2-4 wells of a 96 well plate (e.g., about 10,000 cysts per brain and about 100 bradyzoites per cyst so $10^6$ bradyzoites per brain; infect with $3×10^5$ bradyzoite).
8. Remove the media from the monolayer and add the enteroid medium containing Bradyzoites. The bradyzoites are pre-treated with a bile acid, e.g., an acid of taurine or glycine, such as taurocholic acid, at a concentration of about 0.05 to about 2.5 μM, e.g., about 2 μM, under low oxygen conditions, e.g., less than about 21% oxygen, e.g., about 1% oxygen, or under anaerobic conditions, for up to 20 hours, e.g., up to 4 to 6 hours, then collected, e.g., via centrifugation which also removes the bile acid, and then mixed with the enteroid medium before contact with the monolayers.

9. Monolayers in 50-200 uM linoleic acid are then infected with these bradyzoites and incubated under normal or low oxygen conditions.
10. Intracellular oocysts can be visualized after 5-7 days using the DAPI channel using a fluorescence microscope.

Oocyst Sporulation

1. The infected tissue containing intracellular oocysts is scraped and the host cells are lysed using a 25.8 G needle.
2. Spin at 1200×g @ RT for 10 minutes; the oocysts are in the pellet.
3. Resuspend the pellet in 5 mL of a 2.5% potassium dichromate solution and let it rotate for seven days (4) RT;
4. As an alternative protocol the pellet can also be resuspended in 2% sulfuric acid or resuspending in saline with antibiotics for 7 to 14 days.

Methods

Ethics Statement. Mice were treated in compliance with the guidelines set by the Institutional Animal Care and Use Committee (IACUC) of the University of Wisconsin School of Medicine and Public Health (protocol #M005217). Cats were treated in compliance with the guidelines set by the IACUC of the United States Department of Agriculture, Beltsville Area (protocol P15-017). Both institutions adhere to the regulations and guidelines set by the National Research Council.

Intestinal organoids. Cat intestinal organoids were established from jejunum sections obtained from fetal small intestinal sections. Mouse intestinal organoids were established from jejunum sections from 8-week-old C57BL/6J male mice. Organoids were generated as described in Munera et al. (2017). Briefly, intestinal sections were washed in ice cold PBS containing 0.1 mg/mL streptomycin and 100 U/mL penicillin for 20 minutes. Sequentially. EDTA (Sigma) was added to a final concentration of 2 mM and the tissue incubated for 40 minutes at 4° C. The tissue was then rinsed in cold PBS without EDTA and vigorously shaken until crypts were seen in the supernatant. The crypt suspension was filtered using a 70 μm cell strainer and the crypts were centrifuged at 80×g for 5 minutes. The cells were resuspended in Matrigel (BD Biosciences), pipetted into a 24 well plate, allowed to polymerize and then covered with organoid medium. The organoid medium contains Advanced DMEM/F12 with 2 mM Glutamax, 20 mM HEPES, 1×B27, 1×N2, 10% v/v Fetal bovine serum, 10 mg/L Insulin, 5.5 mg/L Transferrin, 0.67 mg/L Selenite, Penicillin and Streptomycin (all from Invitrogen), 50 ng/ml human EGF (R&D systems), 10 mM Nicotinamide (Sigma), 3 μM CHIR99021 and 10 μM Y-27632 (both Selleckchem) and 50% v/v conditioned medium obtained from L-WRN cell line (ATCC CRL 3276). The medium was changed every other day and the organoids were expanded by passing the cells through a 25 gauge needle every week. A11 experiments were done with cells at passage 2 to 5 and cells were regularly checked for mycoplasma contamination (MicoAlert Lonza).

Intestinal monolayers and fatty acid supplementation. Monolayers were generated from intestinal organoids as described in Methods in Molecular Biology (2017). Briefly, established cat or mouse intestinal organoids were washed with cold PBS, digested by 0.05% trypsin for 5 minutes at 37° C., centrifuged at 250×g for 3 minutes and resuspended in fresh pre-warmed organoid medium. Cell suspension was added into a chamber slide (Thermo) pre-coated with Entactin-Collagen IV-Laminin (Corning) for cat cells or 2% m/v Gelatin in PBS (Sigma) for mouse cells. The slides were coated by air drying the basement membrane matrix or gelatin to air dry overnight. The monolayers were grown for 10-15 days prior to infection with *T. gondii* bradyzoites, with media change every other day until cells reached 90% or more confluency. Linoleic acid or oleic acid conjugated to BSA (Sigma) was added to the organoid monolayers to 0.2 mM 24 hours prior to infection.

Bradyzoite preparation and infection. C57BL/6J mice were oral gavage infected with 500-1000 ME49 oocysts from cat feces. At 28 days postinfection, brains were removed, washed in cold PBS and homogenized with a glass tissue grinder. The suspension was centrifuged at 400×g for 10 minutes and the pellet suspended in 20% m/v Dextran (Average MW 150,000, Sigma). Bradyzoite cysts were pelleted and separated from brain material by centrifugation at 2200× g for 10 minutes. The pellet was washed in PBS, digested by 0.1 mg/mL pepsin in HCl for 5 minutes at 37°, then neutralized with an equal volume 1% Sodium Carbonate (Sigma). Bradyzoites were spun at 250×g for 265 10 minutes, resuspended in pre-warmed organoid medium and added onto the organoid monolayers with a multiplicity of infection of 1 bradyzoite: 10 intestinal epithelial cells (MOI 1:10).

Delta-6-desaturase inhibition. SC 26196 (Cayman) was solubilized in DMSO and used at 20 μM in mouse organoid monolayers. For in vivo treatment, the inhibitor was solubilized in 0.5% m/v methylcellulose and the mice were given 50 mg/kg every 12 hours by oral gavage (He et al., 2012). 4-week old C57BL/6J female mice deleted in Z-DNA-binding protein (Pittman et al., 2016) were divided into four different groups: uninfected control, *T. gondii*-infected without fatty acid supplementation, *T. gondii* infected with linoleic acid supplementation, and *T. gondii*-infected with linoleic acid and SC 26196 inhibitor. Each mouse supplemented with linoleic acid received 10 μL of 99% linoleic acid oil (MilliporaSigma Cat #843483) suspended in 0.5% Methylcellulose per day by oral gavage. Mice were infected with 1000 brain cysts purified as described above by oral gavage and euthanized 7 days post infection. Sample size was at least 2 mice per group and the experiment was repeated 5 times. Alternatively, each mouse was infected with one mouse brain at least 2 months postinfection with at least 1000 cysts. Mice were treated with SC 26196 until day 5 postinfection. Feces were collected from days 5-14 and oocysts enumerated by microscopy.

Immunofluorescence. Intestinal organoid monolayers or mouse fecal samples were fixed in 3.7% formaldehyde in PBS for 20 minutes, permeabilized with 0.2% triton X-100 (Sigma) in PBS at room temperature for one hour and then blocked with 3% BSA in PBS at room temperature for one hour. Primary antibody was incubated at 4° C. overnight in 0.2% v/v Triton x-100 and 3% BSA in PBS (1:100 mouse anti-GRA11B, 1:100 rabbit anti-BRP1, 1:100 mouse anti-AO2, 1:50 monoclonal mouse anti-ZO1 (Santa Cruz) or 1:25 mouse 288 IgM anti-oocyst wall 3G4. Sporulated oocysts from mouse feces were dried onto slides, fixed and permeabilized with ice cold acetone for 30 minutes and incubated with 1:20 mouse 4B6 to the visualize the sporocyst. Slides were incubated one hour with the specific secondary antibody (1:500 goat anti-rabbit Alexa Fluor 488 and 1:500 goat anti-mouse Alexa Fluor 594) at room temperature for one hour and then washed 3 times with PBS. Cells nuclei were stained with 10 μM DAPI (Sigma). Slides were mounted in Vectashield antifade mounting medium (VectorLabs). Samples were imaged on Zeiss Axioplan III equipped with a triple-pass (DAPI/fluorescein isothiocyanate [FITC]/Texas Red) emission cube, differential interference contrast optics, and a monochromatic Axiocam camera operated by Zen software (Zeiss) and processed using ImageJ (Fiji packet).

Tissue sectioning and histology. Ileums were fixed in 3.7% formaldehyde in PBS overnight, embedded in paraffin and sectioned by the Translational Research Initiatives in Pathology laboratory at the University of Wisconsin-Madison. The sections were stained with hematoxylin & eosin (Fischer).

Real-time PCR on ileum cDNA. Z-DNA binding protein deletion mice ice with and without delta-6-desaturase inhibitor treatment were euthanized 7 days post infection. The ileum of each mouse was removed and homogenized in 1 mL of TRIzol. Total RNA was isolated according to manufacturer's protocol (Invitrogen) and treated with amplification grade Dnase I. cDNA was generated using the Invitrogen SuperScript III First-Strand Synthesis kit with random hexamer primers. GRA11B and SAG1 were used as markers of sexual and asexual stages, respectively. The *T. gondii* housekeeping gene TUB1A was used to normalize target gene expression. Real-time quantitative PCR was performed using Bio-Rad iTaq Universal SYBR Green Supermix on 311 an Applied Biosystems StepOnePlus Real-Time PCR system. The efficiency of each primer set was calculated from the slope of a 1:10 dilution standard curve of tachyzoite gDNA, where E=10^(−1/slope). The Pfaffl method (Pfaffl, 2001), which accounts for differences in efficiencies, was then used to calculate the relative gene expression of GRA11B and SAG1 per sample, in triplicate. Only wells with one melt curve temperature were used, indicating a single product. Primer sequences were as follows:

TUB1A Forward:
(SEQ ID NO: 1)
5'-GACGACGCCTTCAACACCTTCTTT-3'

Reverse:
(SEQ ID NO: 2)
5'-AGTTGTTCGCAGCATCCTCTTTCC-3'

SAG1 Forward:
(SEQ ID NO: 3)
5'-TGCCCAGCGGGTACTACAAG-3'

Reverse:
(SEQ ID NO: 4)
5'-TGCCGTGTCGAGACTAGCAG-3'

GRA11B Forward:
(SEQ ID NO: 5)
5'-ATCAAGTCGCACGAGACGCC-3'

Reverse:
(SEQ ID NO: 6)
5'-AGCGAATTGCGTTCCCTGCT-3'

Real-time PCR on fecal samples. Fecal samples from the mice with and without delta-6-desaturase inhibitor treatment were collected. gDNA was generated from 0.1 grams of feces from each mouse using the power soil DNA kit (QIAGEN) according to the manufacturer's instructions except that cells were broken by a bead beater instead of a vortex. A standard curve was generated using a dilution series of 101-105 parasites per well amplified using the SAG1 primer set described above, based on a gDNA sample with known parasite quantity. The Ct values were plotted against the log of the parasite numbers. The number of 333 target gene copies in each sample can be interpolated from the linear regression of the standard curve.

$$\text{target gene copy \#} = 10^{\wedge}\frac{\text{Target gene Tc-}y\text{ intercept}}{\text{slope}}$$

Real-time PCR was performed on each sample, in triplicate, using Bio-Rad iTaq Universal SYBR Green Supermix on an Applied Biosystems StepOnePlus Real-Time PCR system. The calculated copy numbers of each sample were normalized based on the ng of nucleic acid used as PCR template. Only wells with one melt curve temperature were used, indicating a single product.

PCR of cat intestinal monolayers. Cat intestinal monolayers were grown in 24-well plates until confluency and then were incubated with either no fatty acid supplementation, 200 μM oleic acid, or 200 μM linoleic acid for 24 hours. The monolayers were infected with ME49 bradyzoites purified from brains of chronic infected mice in duplicate with uninfected monolayers as a negative control. 7 days post-infection, RNA was extracted with TRIzol and cDNA was synthesized as described above. TgAO2 was used as a marker for macrogametes and TgME49_306338 was used as a marker for microgametes. TUB1A was used as an input control using the same primers as above. A cDNA synthesis reaction without the addition of reverse transcriptase was used as a control for genomic DNA contamination. Equivalent amounts of cDNA per sample were used as a template for each PCR reaction, and the products were separated on an acrylamide gel and imaged. Primer sequences were as follows:

TgAO2 Forward:
(SEQ ID NO: 7)
5'-GTCTTGGTTCGTTGAAGGGGCTG-3'

Reverse:
(SEQ ID NO: 8)
5'-CGTCCTCGATGCCCATGAAATCTG-3'

TgME49_306338 Forward:
(SEQ ID NO: 9)
5'-CCACGTCCTTCGCCGATG-3'

Reverse:
(SEQ ID NO: 10)
5'-CATCAGAGGTCCCAGGTTGTCG 357-3'

Statistical methods. All real-time PCR fecal samples were run in triplicate technical replicates. The difference between the mean target gene copy numbers was analyzed by two-tailed unpaired t tests. The real-time PCR intestinal samples were run in triplicate from two biological replicates per group. The difference between the mean relative expression of each target gene was analyzed by two-tailed unpaired t tests.

Oocyst sporulation and mouse infections. Fresh fecal samples were obtained from each mouse, homogenized in PBS and then centrifuged at 1500× g. The pellet was resuspended in PBS plus penicillin and streptomycin and the samples were shaken for 7 to 14 days at room temperature in presence of oxygen. Mice oocysts were stable for at least 3 months at 4° C. Naïve mice were infected with approximately 250 mouse oocysts through intraperitoneal injection. Blood samples from BALB/c and C57BL/6 mice infected with mouse oocysts were drawn at day 13 and 19 post infection, respectively.

Western immunoblot. ME49 tachyzoite lysates were run on a 15% SDS-PAGE protein gel, transferred to a nitrocellulose membrane and strips blocked with 5% w/v low fat milk in TBS 0.1% v/v Tween-20. Collected serum was diluted. 1:250 TBS 0.1% v/v Tween-20 and 1:2000 anti-mouse HRP was used as the secondary antibody. Serum from chronically infected NMRI and C57BL/6 were used as positives controls, serum from uninfected NMRI and C57BL/6 were used as negative controls. Stripes were imaged by LI-COR (LI-COR Biosciences) on white light or chemiluminescence for 2 or 5 min exposures.

Results and Discussion

Figure 2:
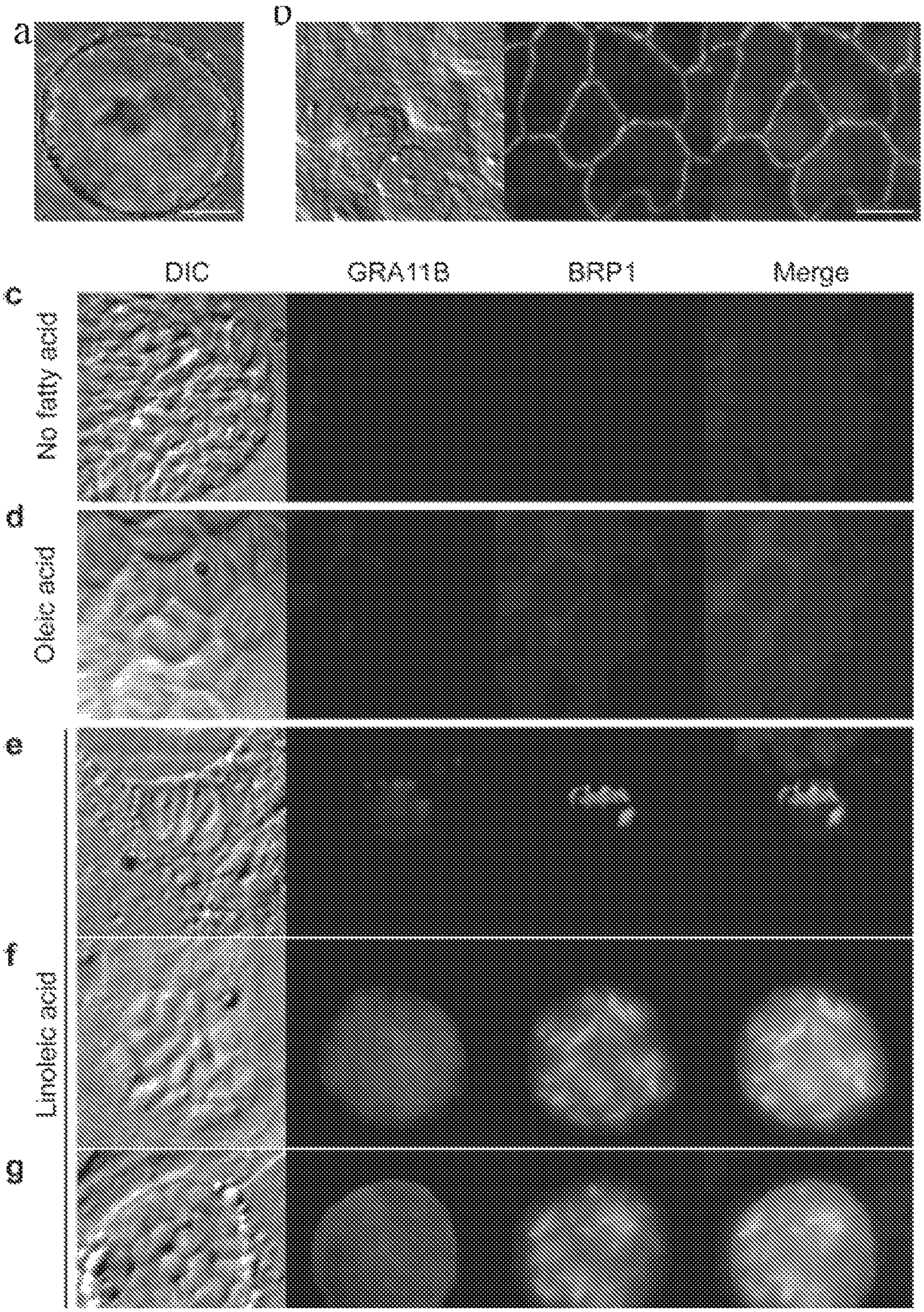
FIGS. 2A-G. Linoleic acid enhances progression through the sexual stages. A) Cat intestinal organoids were generated from small intestine sections and were grown in basement membrane matrix. Example of a growing organoid, 100 μm size bar. B) Intestinal organoids were dissociated using trypsin and single cells seeded onto glass coverslips to grow as monolayers. The cells in the monolayer expressed the tight junction protein ZO-1 (green), 20 μm size bar. Cat intestinal monolayers were incubated with either C) no fatty acid supplementation, D) 200 μM oleic acid, or E), F), G) 200 μM linoleic acid for 24 hours, then infected with ME49 bradyzoites for 5 days. Parasites undergoing sexual development were commonly seen only with linoleic acid supplementation as marked by staining with GRA11B (red) or BRP1 (green). Parasites in E), early, F), middle or G), late stages of sexual development were noted by differential 189 localization of GRA11B. All panels are 20 μm square with a 5 μm white size bar in the lower right corner.
Figure 6:
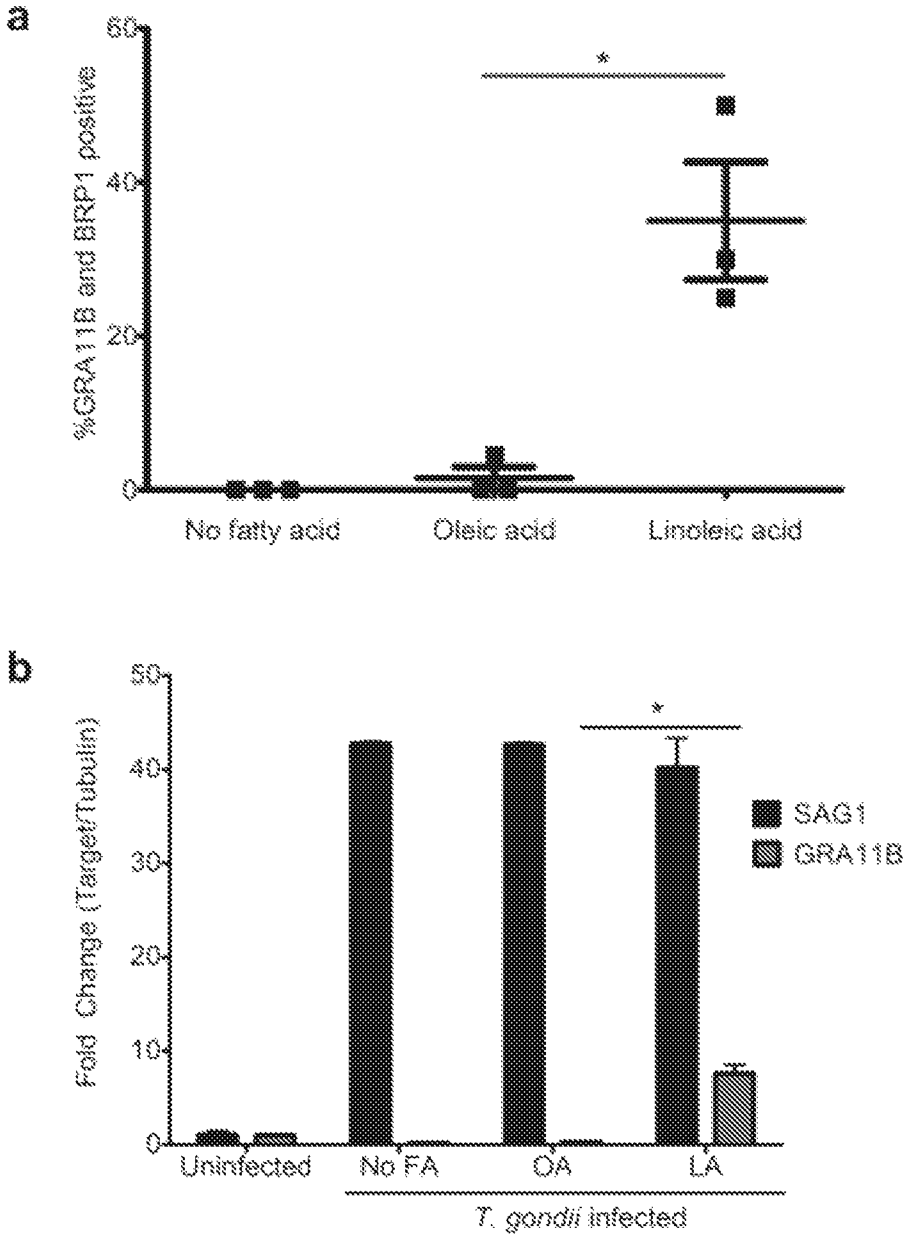
FIGS. 6A-B. Quantification of merozoites in cat tissue culture. A) Cat intestinal organoids were disassociated by trypsin then grown as monolayers on glass slides. Slides were divided into three different groups: not supplemented with fatty acid, supplemented with 200 μM oleic acid or supplemented 200 μM linoleic acid. Monolayers were infected with *T. gondii* MEM bradyzoites purified from brains of chronic infected mice at a 1:10 MOI. Five days after infection, staining for GRA11B and BRP1 along with DAPI, allowed the percentage of vacuoles positive for GRA11B and BRP1out of the total vacuoles was determined. Total number of parasitophorous vacuoles were counted by positive DAPI staining and confirmed by morphology with DIC. At least 50 parasitophorous vacuoles were counted per replicate. Three biological replicates were counted and on average 35% of the total vacuoles were positive far both GRA11B and BRP1 in the linoleic acid supplemented monolayers. *p-value=0.0126 with N=3 by two-tailed unpaired t test. Straining for both BRP1 and GRA11B was used to ensure that merozoite stages were counted. RNAseq and immunofluorescent imaging of the cat intestinal epithelium shows that GRA11B is exclusively expressed in merozoites. BRP1 is a rhoptry protein that was initially found in bradyzoites; however, it is also expressed in merozoite. B) Cat intestinal monolayers were grown as described in panel A, except monolayers were quenched by TRIzol 5 days post-infection, RNA was extracted, and cDNA was synthesized using an oligo (dT) primer to amplify mRNA, Expression of SAG1 and GRA11B were quantified by qPCR and the fold change calculated in comparison with uninfected cells. TUB1A was used to normalize gene expression across samples. GRA11B expression was significantly more abundant in the linoleic acid supplemented monolayers with two biological replicates. *p-value=0.0155 with N=2 by two-tailed unpaired t test.

To determine the molecular mechanisms that define the species specificity of *T. gondii* sexual development, cat intestinal organoids were generated (FIG. 2A), then these epithelial cells were seeded onto glass coverslips. These monolayers displayed intestinal epithelial properties, including polarization and tight junction formation (FIG. 2B). To simulate natural infection, *T. gondii* was harvested from mouse brains 28-40 days after primary infection and the parasites were released from the brain cysts by pepsin and acid digestion. After neutralization with sodium carbonate, parasites were seeded onto the cat intestinal monolayers, incubated for five days, and stained for markers of the parasite pre-sexual stage called a merozoite (Ramakrishnan et al., 2017; Schwarz et al., 2005). While occasional GRA11B and BRP1 staining was observed, the vast majority of the culture was negative for these merozoite markers (FIG. 2C), suggesting that a required nutrient was limiting under these culture conditions. Because recent studies showed that the *T. gondii* asexual stages scavenge fatty acids, particularly oleic acid, from the host (Nolan et al., 2017) and that sexual development of many fungi is dependent on linoleic acid (Brown et al., 2008), it was surmised that supplementation with these fatty acids could facilitate *T. gondii* sexual development. 200 μM oleic or linoleic acid was added to cat intestinal monolayer culture medium 24 hours prior to infection 63 with *T. gondii*. After 5 days of infection, it was found that the addition of linoleic acid but not oleic acid caused approximately 35% of the *T. gondii* to express both merozoite stage markers (FIG. 6A). As seen in in vivo cat intestine, GRA11B changes localization from within the parasite dense granule organelles in the early stages of development to the parasitophorous vacuole and parasitophorous vacuole membrane in later stages of development (Ramakrishnan et al., 2017). Similar localization of GRA11B was observed depending on vacuole size, likely representing early, middle and late stages (FIGS. 2E-G). BRP1 has previously been localized to the rhoptry organelles in the apical end of the merozoite (Schwarz et al., 2005), similar to the structures we see in FIGS. 2E-G.

Figure 7:
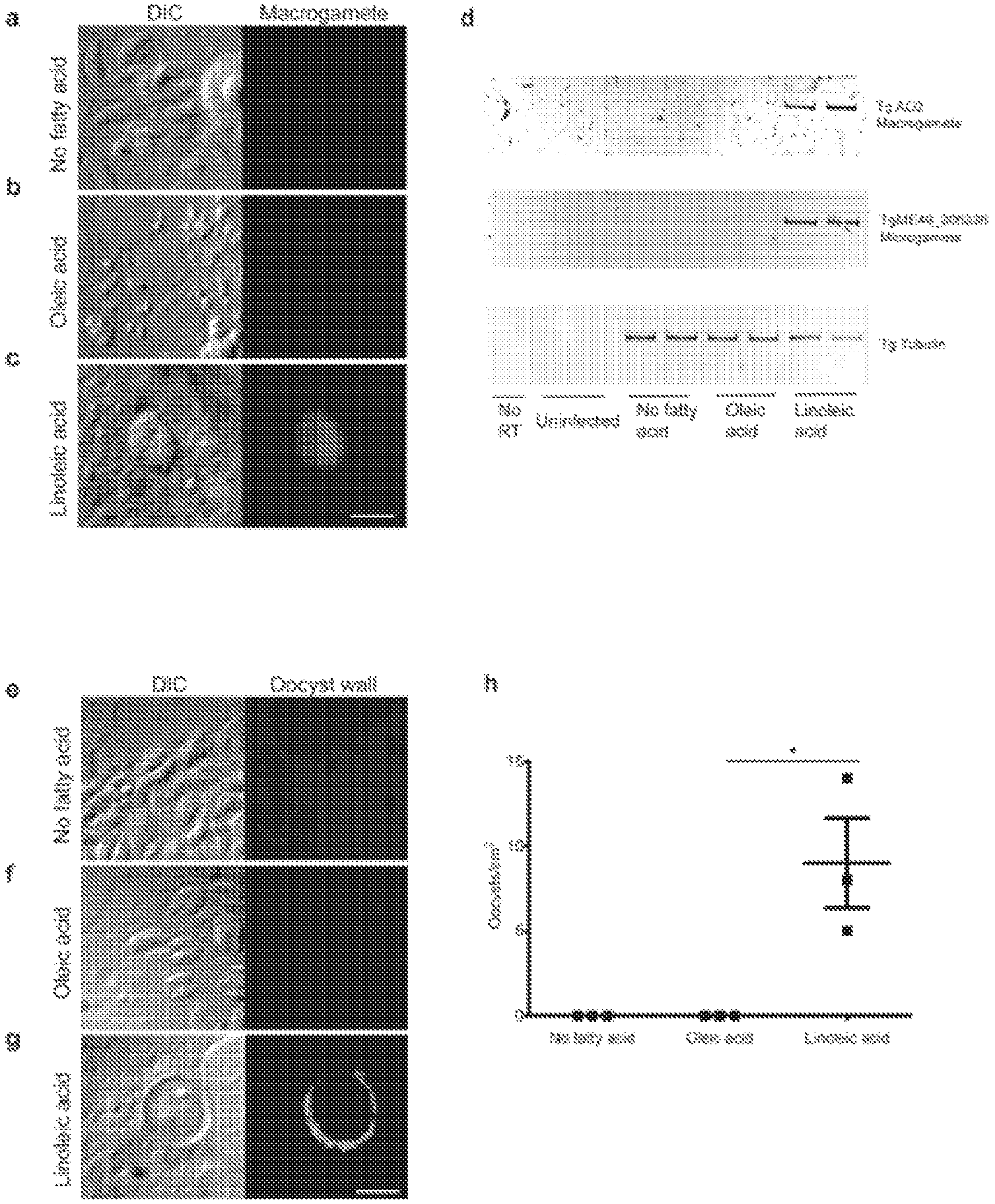
FIGS. 7A-H. Identification of gametes and intracellular oocysts in cat tissue culture. Cat intestinal organoids were disassociated by trypsin then grown as monolayers on glass slides. Monolayers were grown to confluency and then were incubated with either no fatty acid supplementation (A and E), 200 μM oleic acid (B and F), or 200 μM linoleic acid (c and g) for 24 hours and infected with ME49 bradyzoites purified from brains of chronic infected mice. After 7 days, monolayers were incubated with mouse anti-AO2 (panels A-C) or mouse monoclonal IgM 3G4 (panels E-G), The amiloride-sensitive amine oxidase, copper-containing protein 2 (AO2) is an enzyme exclusively expressed in macrogametes and early oocysts and has a possible role in oocyst wall biogenesis. AO2 expression was only detected by immunofluorescence in the monolayers supplemented with linoleic acid (panel C). 3G4 is a mouse monoclonal antibody produced by immunizing mice with purified oocyst walls, thus it is a marker of oocyst wall biogenesis. Only monolayers supplemented with linoleic acid (G) had positive 3G4 vacuoles. All panels are 20 μm square with a 5 μm white size bar in the lower right corner. D) Markers for macrogamete and microgamete expression were also evaluated by PCR. Cat intestinal monolayers were grown in 24-well plates until confluency and then infected with *T. gondii* bradyzoites in duplicate using the same conditions as above. 7 days post-infection, RNA was extracted with TRIzol and cDNA was synthesized using an oligo (dT) primer to only amplify mRNA. AO2 was again used as a marker for macrogametes and the expected PCR product is 218 bp. To assess microgamete presence, we selected the gene TgME49_306338, which is overexpressed in the gametes stage, corresponded to day 7 post-infection in cats and has 44% identity to a protein expressed in the flagella of the motile green algae *Chlamydomonas reinhardtii*. The expected PCR product for TgME49_306338 is 160 bp. TUB1A was used as an input control and results in a 172 bp product. NO RT corresponds to a cDNA synthesis reaction without the addition of reverse transcriptase (RI) as a control for genomic DNA contamination. Equivalent amounts of cDNA per sample were used as a template for each PCR reaction, and the products were separated on an acrylamide gel. Bands with the correct size showing AO2 and TgME49_306338 expression were only observed in linoleic acid supplemented monolayers. H) The number of positive oocyst walls stained with 3G4 were quantified. Cat intestinal monolayers were infected with *T. gondii* bradyzoites and after 7 days fixed with 3.7% formaldehyde in PBS and incubated with 3G4 as showed in the panels e, f and g. The number of positive oocyst walls were counted in each slide and divided by the area of slide in $cm^2$. The number of positive oocysts walls in monolayers supplemented with linoleic acid was significantly higher than supplementing with oleic acid in three biological replicates. *p-value=0.0272 with N=3 by two-tailed unpaired t test.

Within the feline intestine, merozoites are known to differentiate into micro- and macrogametes that fuse to become diploid oocysts. After 7 days of infection, round structures were seen with reactivity to the macrogamete protein AO210 in cat intestinal monolayers cultured with 200 μM linoleic acid but not in unsupplemented or oleic acid-supplemented cultures (FIGS. 7A-C). PCR of these day 7 linoleic acid supplemented cultures amplified message for AO2 as 78 well as the predicted microgamete flagellar dynein motor protein TGME49_306338 with 44% identity to the homologue from the motile green alga *Chlamydomonas reinhardtii* (FIG. 7D). In parallel, the presence of intracellular oocyst wall biogenesis was assessed in these linoleic acid supplemented cat cells by using the 3G4 antibody (Dumètre & Dadè that which recognizes the *T. gondii* oocyst wall. There were approximately 9 oocyst walls per $cm^2$ of cultured cat cells with supplemented with 200 μM linoleic acid but none in not supplemented or oleic acid supplemented cultures (FIGS. 7E-H). Addition of 20 μM linoleic acid did not enhance oocyst wall production, indicating that the concentration of linoleic acid was critical for proper development.

Figure 3:
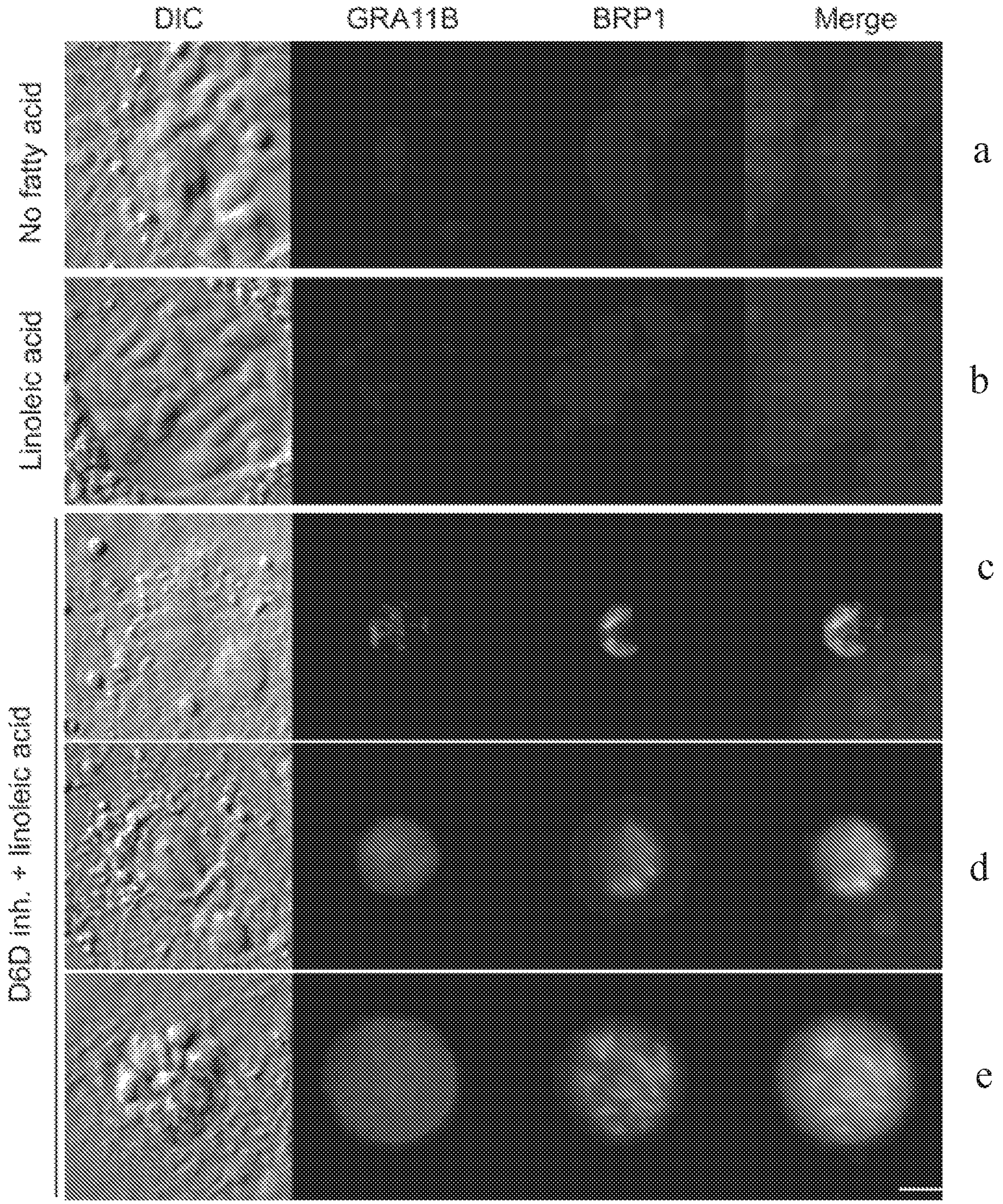
FIGS. 3A-E. Inhibition of delta-6-desaturase permits sexual development in mouse culture. Mouse intestinal monolayers were incubated with either A), no fatty acid supplementation, B) 200 μM linoleic acid or C), D), E), 200 μM linoleic acid plus the delta-6-desaturase inhibitor SC26196 for 24 hours, then infected with ME49 bradyzoites for 5 days. Only in cultures supplemented with linoleic acid and SC26196 were parasites undergoing sexual development detected by staining with GRA11B (red) or BRP1 (green). Parasites in C), early, D), middle, or E), late stages of development were noted by differential localization of GRA11B. All 198 panels are 20 μm square with a 5 μm white size bar in the lower right corner.
Figure 8:
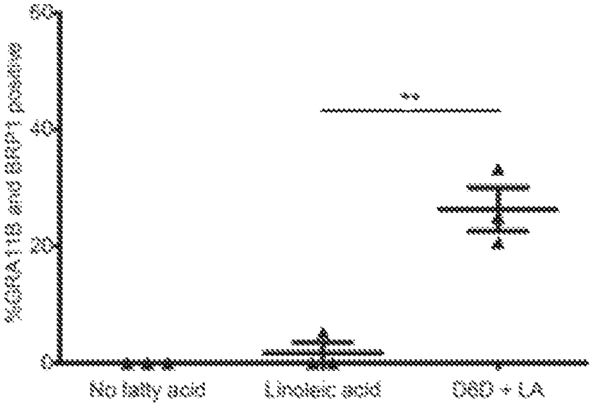
FIG. 8. Quantification of merozoites in mouse tissue culture. Mouse intestinal organoids were disassociated by trypsin and the individual cells were grown on glass slides. Slides were divided into three different groups: not supplemented with fatty acids or SC26196 inhibitor, supplemented with 200 μM Linoleic acid, or supplemented with 200 μM Linoleic acid plus the addition of 20 μM SC26196 in DMSO (delta-6-desaturase inhibitor). Equal volumes of DMSO was added to all conditions. Monolayers were infected with *T. gondii* ME49 bradyzoites purified from brains of chronic infected mice. At 5 days post-infection, monolayers were stained for GRA11B, BRP1 and DAPI. Total number of parasitophorous vacuoles were counted by positive DAPI staining and confirmed by morphology with DIC. At least 50 parasitophorous vacuoles were counted per replicate. The percentage of vacuoles positive for GRA11B and BRP1 out of the total vacuoles was determined. Three biological replicates were counted and on average 26% of the total vacuoles were positive for GRA11B and BRP1 in the linoleic acid supplemented monolayers with the addition of SC 26196. **p-value=0.0039 with N=3 by two-tailed unpaired t test.

The dependence of *T. gondii* sexual development on high levels of linoleic acid was intriguing because cats are the only mammal known to lack delta-6-desaturase activity in their small intestines (Rivers et al., 1975; Sinclair et al., 1979). Delta-6-desaturase is the first and rate-limiting step for the conversion of linoleic acid to arachidonic acid. Linoleic acid is the dominant fatty acid in cat serum, comprising 25-46% of the total fatty acid (MacDonald et al., 1983; Trevizan et al., 2012; Hall et al., 2013; Fujiwara et al., 2015), whereas rodents serum contains only 3-10% linoleic acid (Navarro et al., 1992; Adan et al., 1999; Sato et al., 2004; Jelińska et al., 2017). It was hypothesized that the lack of delta-6-desaturase activity in the cat small intestine allows for a buildup of linoleic acid from the diet, which then acts as a positive signal for *T. gondii* sexual development. To test this hypothesis, mouse intestinal monolayers were infected, with *T. gondii* and supplemented them with linoleic acid and the chemical SC26196, a specific inhibitor of the delta-6-desaturase enzyme, to establish high steady-state levels of linoleic acid (Obukowicz et al., 1998). Five days after infection of the mouse culture with *T. gondii*, merozoite markers BRP17 and GRA11B6 were assessed. Expression of GRA11B and BRP1 was observed in mouse intestinal cells only when supplemented with both linoleic acid and SC26196 (FIG. 3). These data suggest that the delta-6-desaturase enzyme must be inhibited in order for high enough levels of exogenous linoleic acid to increase and induce *T. gondii* sexual development in non-feline intestinal cells. Similar to cat cells, mouse intestinal monolayers supplemented with both linoleic acid and SC26196 had approximately 26% of the *T. gondii* vacuoles expressing both BRP1 and GRA11B (FIG. 8).

Figure 4:
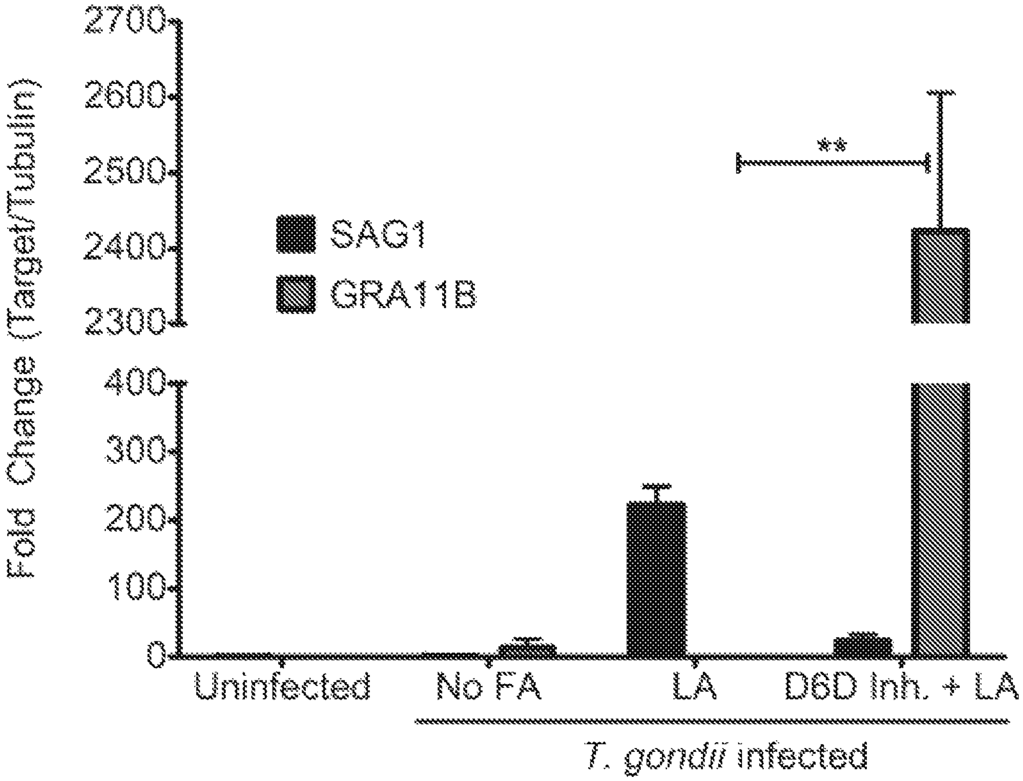
FIGS. 4A-C. Z-DNA binding protein knock out mice shed oocysts after inhibition of delta-6-desaturase. Mice were gavage fed linoleic acid and the delta-6-desaturase inhibitor SC26196 12 hours prior to infection with ME49 bradyzoites, and then every 12 hours for the 7 days of infection. A) qPCR of cDNA from the ileum for tachyzoite marker SAG1 (black) and GRA11B (red) shows that GRA11B is significantly up regulated only in the presence of SC26196 (p-value=0.0057 with N=2 by two tailed unpaired t test). B), C), Ileum sections an day seven postinfection were paraffin embedded and stained with hematoxylin & eosin to visualize pre-sexual stages.
Figure 4:
Figure 4:
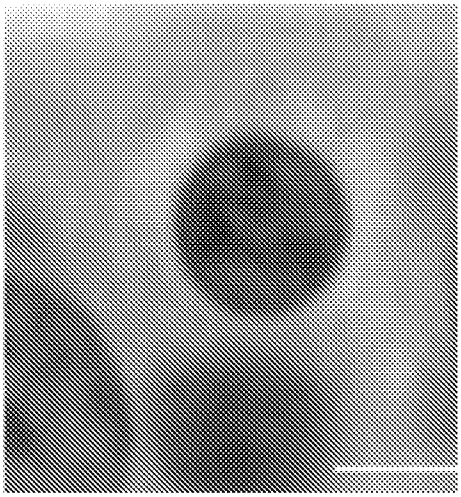

Oocysts excreted in cat feces must undergo a sporulation process to become infectious to the next host. In an attempt to sporulate the round structures containing oocyst wall antigen that were derived from either cat or inhibited mouse cultured intestinal cells, they were kept at room temperature with aerosolization for 7-14 days. Unfortunately, few structures were obtained from the monolayers, they did not appear to sporulate and they were not infectious to mice. It was hypothesized that *T. gondii* oocyst development and infectivity may require physiological conditions in a whole animal that could not necessarily be recapitulated in tissue culture. To test this hypothesis, delta-6-desaturase activity in the intestines of live mice was inhibited. The delta-6-desaturase inhibitor SC26196 is effective as an anti-inflammatory agent in whole animal experiments (He et al., 2012). Because it was previously seen that sporozoites shifted to the rapidly replicating asexual stage called a tachyzoite within eight hours after the oral inoculation into rats (Guiton et al., 2017), the mice were fed a linoleic acid rich diet and pretreated them with the delta-6-desaturase inhibitor SC26196 (or a no-inhibitor control) 12 hours prior to oral infection with *T. gondii* and every 12 hours thereafter. In mice fed both the linoleic acid-rich diet and the SC26196 inhibitor, seven days after infection, qPCR of ileum cDNA showed high expression of the *T. gondii* merozoite marker GRA11B and low expression of the asexual tachyzoite stage marker SAG1 (Burg et al., 1988) (FIG. 4A, and Table 2). Ileum sections on day sewn postinfection were paraffin embedded and stained with hematoxylin & eosin. Pre-sexual and early oocysts stages were present only in the tissue of mice fed linoleic acid and the delta-6-desaturase inhibitor (FIGS. 4B-C).

TABLE 2

Raw Ct values of the TUB1A, SAG1, and GRA11B standard curves on a dilution series of gDNA from tachyzoites and raw Ct values of TUB1A, SAG1, and GRA11B from the cDNA of homogenized mouse ileum samples using UB1A as the normalizer for target gene expression. Wells with multiple melt curve temperatures, indicating off target products, were excluded (NA). Samples below the detection limit of 40 cycles are labeled BDL.

| | Tubulin standard curve | | |
|---|---|---|---|
| dilution | Replicate 1 | Replicate 2 | Ct mean |
| 1 | 27.6488323 | 27.5695381 | 27.6091852 |
| 10 | 29.975256 | 30.1574116 | 30.0663338 |
| 100 | 31.9853363 | 32.1811714 | 32.0832539 |
| 1000 | 34.956852 | 34.8546867 | 34.9057693 |

| | SAG1 standard curve | | | GRA11B standard curve | | |
|---|---|---|---|---|---|---|
| dilution | Replicate 1 | Replicate 2 | Ct mean | Replicate 1 | Replicate 2 | Ct mean |
| 1 | 31.2750359 | 31.8404484 | 31.5577421 | 25.4644253 | 24.1681748 | 24.81630005 |
| 10 | 33.1405373 | 33.563591 | 33.3520641 | 25.9054524 | 29.3562576 | 27.63085500 |
| 100 | 36.9525986 | 35.9841347 | 36.4683666 | 28.6691532 | 32.2224998 | 30.4458265 |
| 1000 | NA | NA | | 35.1540375 | 31.3671227 | 33.2605801 |

TUB1A raw Ct values

| | Uninfected | | No fatty acid | | Linoleic acid | | D6D Inh + LA | |
|---|---|---|---|---|---|---|---|---|
| | Mouse 1 | Mouse 2 | Mouse 1 | Mouse 2 | Mouse 1 | Mouse 2 | Mouse 1 | Mouse 2 |
| 1 | 32.5138321 | 31.4240837 | 31.1165199 | 31.2665482 | 33.4409027 | 31.9599762 | 31.3773556 | 32.3561516 |
| 2 | 32.3842278 | 31.6126347 | 31.1024532 | 31.4534149 | 33.1783142 | 31.9191761 | 31.573513 | 32.0675926 |
| 3 | 32.074028 | 31.6512508 | 31.0960255 | 29.94104 | 32.9809799 | 31.8425732 | 31.4610386 | 33.3344841 |
| Ct mean | 32.3240293 | 31.5626564 | 31.1049995 | 30.887001 | 33.2000656 | 31.9072418 | 31.4706357 | 32.5860761 |

SAG1 raw Ct values

| | Uninfected | | No fatty acid | | Linoleic acid | | D6D Inh + LA | |
|---|---|---|---|---|---|---|---|---|
| | Mouse 1 | Mouse 2 | Mouse 1 | Mouse 2 | Mouse 1 | Mouse 2 | Mouse 1 | Mouse 2 |
| 1 | BDL | 36.8367805 | 34.7008286 | 35.866993 | 32.6290741 | 31.5208263 | 33.0942078 | 34.7215462 |
| 2 | BDL | BDL | 35.1256409 | 36.7775307 | 32.3070946 | 31.460474 | 32.4105225 | 35.8192787 |
| 3 | BDL | BDL | 36.6918411 | 35.9931984 | 32.9669876 | 31.7187042 | 33.5042496 | 34.502491 |
| Ct mean | 40 | 36.8367805 | 35.5061035 | 36.212574 | 32.6343854 | 31.5666682 | 33.0029933 | 35.0144386 |

GRA11B raw Ct values

| | Uninfected | | No fatty acid | | Linoleic acid | | D6D inh + LA | |
|---|---|---|---|---|---|---|---|---|
| | Mouse 1 | Mouse 2 | Mouse 1 | Mouse 2 | Mouse 1 | Mouse 2 | Mouse 1 | Mouse 2 |
| 1 | BDL | BDL | 29.9149323 | 30.7989769 | NA | 33.4278946 | 22.2784882 | 23.7081032 |
| 2 | BDL | BDL | 31.2883797 | 31.8176823 | 36.0228119 | 35.5871048 | NA | 24.4187279 |
| 3 | 34.8929062 | BDL | 24.8837833 | 31.6775894 | 38.2405396 | 39.0534363 | 25.175827 | 26.4390202 |
| Ct mean | 34.8929062 | 40 | 28.6956984 | 31.4314162 | 37.1316757 | 36.0228119 | 23.7271576 | 24.8552837 |

As early as day six postinfection, oocyst-like structures showing 3G4 antibody-positive staining were present in the mouse feces (FIG. 9A) and increased in number until day seven when the mice were sacrificed. qPCR on genomic DNA from mouse fecal samples showed that *T. gondii* genomic DNA was detectable only in mice treated with SC26196 (FIG. 4A, and Table 3), indicating that delta-6-desaturase must be inactivated in mice for *T. gondii* sexual stages to develop in the mouse gut. Mice produced 1000-10,000 oocysts/gram dry feces. To increase the number and duration of oocysts shedding, mice were fed the SC2696 inhibitor every 12 hours only until day 5 postinfection. Oocysts were monitored in the feces with the peak of shedding being days 8-9 with between 100,000450,000 oocysts/gram dry feces (FIG. 5B), which is within the range seen for cats, 2000-1,500,000 oocysts/gram of feces (Dabritz & Conrad, 2010; Zulpo et al., 2018).

TABLE 3

Raw Ct values of the SAG1 standard curve on a dilution series of gDNA with known parasite quantity and raw Ct values of SAG1 amplification from gDNA of unknown fecal samples using ng quantity input as the normalizer. Wells with multiple melt curve temperatures, indicating off target products, were excluded (NA).

| SAG1 standard Curve | | | |
|---|---|---|---|
| Parasites/ well | 1 | 2 | Ct mean |
| 1E+01 | 35.57521432 | 33.1639857 | 34.3696 |
| 1E+02 | 31.37476921 | NA | 31.37477 |

TABLE 3-continued

Raw Ct values of the SAG1 standard curve on a dilution series of gDNA with known parasite quantity and raw Ct values of SAG1 amplification from gDNA of unknown fecal samples using ng quantity input as the normalizer. Wells with multiple melt curve temperatures, indicating off target products, were excluded (NA).

| | | | |
|---|---|---|---|
| 1E+03 | 27.49031258 | 27.3771229 | 27.43372 |
| 1E+04 | 24.34825134 | 24.4016438 | 24.37495 |
| 1E+05 | 21.08660126 | 20.9996948 | 21.04315 |

SAG1 raw Ct values

| | Uninfected | No fatty acid | Linoleic acid | D6D Inh. + linoleic acid |
|---|---|---|---|---|
| 1 | 33.80274963 | 33.11815643 | 37.01938629 | 30.21689415 |
| 2 | 34.18164825 | 33.36447906 | 36.4305954 | 29.94301414 |
| 3 | 34.53059769 | 35.27391434 | 34.07853317 | 29.80986023 |
| Ct mean | 34.17166519 | 33.91884995 | 35.84283829 | 29.98992284 |
| ng/well | 10 | 22 | 14 | 12.5 |

Figure 5:
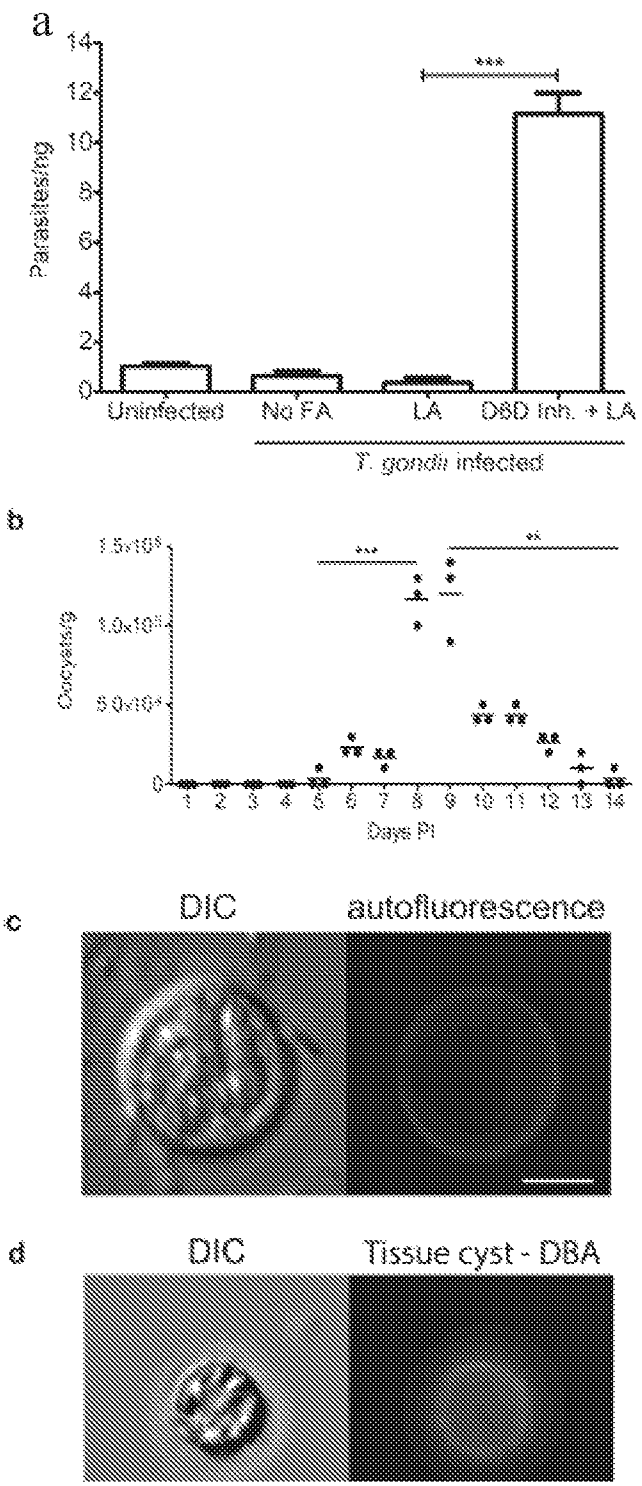
FIGS. 5A-D. Oocysts shed from Z-DNA binding protein knock out mice are infectious. A) qPCR on genomic DNA from mouse fecal samples using SAG1 primers shows that *T. gondii* genomic DNA is detected only in mice treated with SC26196 (p-value=0.0002 with N=3 by two-tailed unpaired t test). B) Counts of the number of oocysts/gram of feces over time. *p-value=0.0003 day 5 vs 8 and p-value=0.0017 day 9 vs 14. c, After 7 days in sporulation conditions, sporocysts were visible by DIC, and blue autofluorescence of the oocyst walls was enhanced. All panels are 20 μm square with a 5 μm white size bar in the lower right corner. D) After 28 days, *T. gondii* cysts can be detected in the brains of mice infected with oocysts as measured by *Dolichos biflorus* agglutinin (Boothroyd et al., 1997) (DBA, red).
Figure 9:
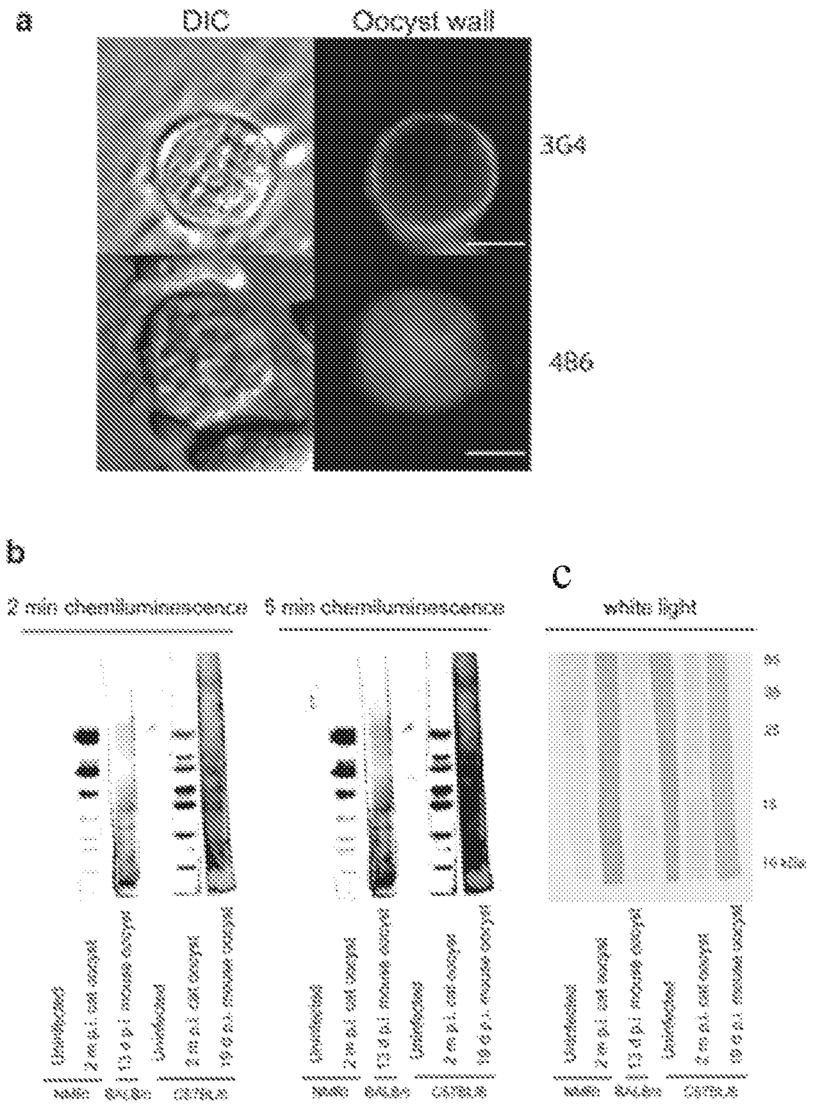
FIGS. 9A-C. Mice oocyst characterization and infectivity evaluation by serum conversion. A) Fresh oocysts were fixed in 3.7% formaldehyde in suspension, incubated with mouse monoclonal antibody 3G4 overnight, then incubated with goat anti-mouse Alexa fluor 488 secondary antibody. Panels are 20 μm square with a 5 μm white size bar in the lower right corner. B) To expose the sporocyst wall to the 4B6 antibody, the sporulated oocysts were dried to the slides, then fixed and permeabilized with cold acetone for 30 minutes, incubated with mouse monoclonal antibody 4B6 overnight then incubated with goat anti-mouse Alexa fluor 488 secondary antibody. All panels are 20 μm square with a 5 μm white size bar in the lower right corner. C) Oocysts collected from SC 26196-treated mice were sporulated as described above and injected intraperitonially into BALB/c and C57BL/6 mice. At 13 or 19 days post-infection (d.p.i.) serum was collected from each mouse. Serum from uninfected mice was used as a negative control. As a positive control, serum samples from NMRI or C57BL/6 mice 2 months post-infection (m.p.i.) with 5000 cat oocysts were used. These serum samples were tested for the presence of antibodies against a *T. gondii* ME49 tachyzoite lysate by western blot. 2 and 5 minute (min) chemiluminescent exposures, as well as a white light image showing the individual lanes used. Positive bands were observed in both BALB/c or C57BL/6 mice, indicating exposure to infectious *T. gondii*. Blots are representative of 3 independent experiments.

*T. gondii* oocysts are susceptible to desiccation, making them unable to sporulate (Dubey et al., 2011). Therefore, the mouse feces or the intestinal contents were promptly placed in saline and sporulated at room temperature with aerosolization. After seven days, sporulation was evident in approximately 50% of the oocysts by visualization of sporozoites, a deep blue autofluorescent wall (Belli et al., 2003) (FIG. 5C), and reactivity with the 4B6 antibody that recognizes the two individual sporocysts within the oocysts (Dumètre & Dardè, 2005) (FIG. 9C). The sporulated oocysts were infectious to mice as seen by serum conversion (FIG. 9C) and cysts in the brains 28 days later (FIG. 5D). Similar to oocysts derived from a cat, these mouse-derived sporulated oocysts were stable and infectious for at least three months when stored at 4° C.

All together, these results define the mechanism of species specificity for *T. gondii* sexual development and show that we can break the species barrier for *T. gondii* sexual development by inhibiting delta-6-desaturase activity in the intestines of a non-feline host. The lack of delta-6-desaturase activity and the build-up of linoleic acid likely enhance *T. gondii* sexual development in multiple ways. First, prior work suggests linoleic acid is cytotoxic for the asexual tachyzoite stage (Shamseddin et al., 2015), thus tachyzoite development would be halted in a linoleic rich environment. Second, inhibition of delta-6-desaturase likely lowers arachidonic acid levels, which would alter the production of immune lipid mediators known as eicosanoids. Finally, and possibly most important, the dramatic difference between oleic acid with one double bond and linoleic acid with two, highlights that linoleic acid is probably used as a signaling molecule and not to meet basic nutritional needs. Quorum-sensing for sexual reproduction in fungi is dependent on oxygenation of linoleic acid but not oleic acid (Brown et al., 2008). The multiple host and *T. gondii* cyclooxygenases and lipoxygenases likely oxygenate linoleic acid to an oxylipin signaling molecule for *T. gondii* sexual development to proceed.

TABLE 4

Raw Ct values of TUB1A, SAG1, and GRA11B from the cDNA of cat intestinal monolayers samples using TUB1A as the normalizer for target gene expression. Wells with multiple melt curve temperatures, indicating off target products, were excluded. (NA). Samples below the detection limit of 40 cycles are labeled BDL.

TUB1A raw Ct values

| | Uninfected | | No fatty acid | | Oleic acid | | Linoleic acid | |
|---|---|---|---|---|---|---|---|---|
| | 1 | 2 | 1 | 2 | 1 | 2 | 1 | 2 |
| 1 | 34.2925758 | 33.6825256 | 24.5713024 | 23.9879074 | 24.2402058 | 22.8974991 | 22.2816677 | 23.2453613 |
| 2 | 34.3980637 | 34.12537 | 24.5229015 | 23.9841576 | 24.2534714 | 22.8809643 | 22.29282 | 23.404686 |
| 3 | 34.0003052 | 34.0256615 | 24.4816723 | 24.0200214 | 24.154562 | 22.9417667 | 22.2845783 | 23.479929 |
| Ct mean | 34.2303149 | 33.944519 | 24.5252921 | 23.9973621 | 24.2160797 | 22.9067434 | 22.2863553 | 23.3766588 |

SAG1 raw Ct values

| | Uninfected | | No fatty acid | | Oleic acid | | Linoleic acid | |
|---|---|---|---|---|---|---|---|---|
| | 1 | 2 | 1 | 2 | 1 | 2 | 1 | 2 |
| 1 | 36.4223297 | BDL | 21.1433277 | 20.662405 | 20.8685226 | 19.6628284 | 19.088089 | 20.0940189 |
| 2 | 37.0707512 | 34.516964 | 21.214653 | 20.5705509 | 20.8812828 | 19.5425129 | 19.1926098 | 19.9284286 |
| 3 | BDL | 36.7298584 | 21.0926743 | 20.6083775 | 20.7492256 | 19.4645195 | 19.1642513 | 19.9467525 |
| Ct mean | 36.7465405 | 35.6234112 | 21.1502183 | 20.6137778 | 20.8330104 | 19.5566203 | 19.1483167 | 19.9897334 |

GRA11B raw Ct values

| | Uninfected | | No fatty acid | | Oleic acid | | Linoleic acid | |
|---|---|---|---|---|---|---|---|---|
| | 1 | 2 | 1 | 2 | 1 | 2 | 1 | 2 |
| 1 | BDL | BDL | 33.2187729 | 33.3933258 | 32.4370689 | 31.769556 | 26.5284595 | 27.6702003 |
| 2 | BDL | BDL | 33.7598324 | 33.9468613 | 32.7270679 | 31.9066696 | 26.3351135 | 27.8152237 |
| 3 | BDL | BDL | 33.6962605 | 33.3205395 | 32.4270611 | 31.7734032 | 26.4439087 | 27.7659969 |
| Ct mean | 40 | 40 | 33.5582886 | 33.5535755 | 32.5303993 | 31.8165429 | 26.4358273 | 27.7504737 |

TABLE 4-continued

Raw Ct values of TUB1A, SAG1, and GRA11B from the cDNA of cat intestinal monolayers samples using TUB1A as the normalizer for target gene expression. Wells with multiple melt curve temperatures, indicating off target products, were excluded. (NA). Samples below the detection limit of 40 cycles are labeled BDL.

| | SAG1 standard curie | | |
|---|---|---|---|
| dilution | Replicate 1 | Replicate 2 | Ct mean |
| 10 | 17.6871128 | 17.7186909 | 17.7029018 |
| 100 | 20.7279301 | 20.6926079 | 20.710269 |
| 1000 | 23.9669991 | 24.6088753 | 24.2879372 |
| 10000 | 27.793478 | 28.4385777 | 28.1160278 |
| 100000 | 30.9016266 | 30.9298096 | 30.9157181 |

| | Tubulin standard curve | | |
|---|---|---|---|
| dilution | Replicate 1 | Replicate 2 | Ct mean |
| 10 | 18.3074322 | 18.3029099 | 18.305171 |
| 100 | 20.5489845 | 21.6764679 | 21.1127262 |
| 1000 | 24.7559052 | 25.7847538 | 25.2703295 |
| 10000 | 28.4486732 | 28.6410675 | 28.5448704 |
| 100000 | 31.6899014 | 31.8466282 | 31.7682648 |

| | GRA11B standard curve | | |
|---|---|---|---|
| dilution | Replicate 1 | Replicate 2 | Ct mean |
| 10 | 14.2530499 | 13.6932898 | 13.9731698 |
| 100 | 16.2970276 | 16.4769402 | 16.3869839 |
| 1000 | 19.4292374 | 19,6002369 | 19.5147371 |
| 10000 | 22.900362 | 22.9935303 | 22.9469461 |
| 100000 | 25.9253998 | 26.5503712 | 26.2378855 |

Example 3

Purification of Oocysts from Fecal Material

Collect fecal material for several days and proceed to oocyst isolation (Upton, 1997). Oocysts are physically separated from fecal material (food particles, other microorganisms, etc.) by extensive washings followed by two flotations. Because this procedure involves large quantities of infectious oocysts, proper biosafeguards should be in place, e.g., use of lab coats and eye goggles, and gloves should be changed frequently. A specific area of the laboratory and specific equipment (e.g. centrifuges) dedicated to this procedure may further minimize exposure and cross contamination risk. To avoid excystation of oocysts, all equipment, solutions, and samples should be maintained at 4° C. or on ice. Ice buckets or other receptacles are filled with ice to hold all samples and solutions. All liquids generated from oocyst purification, including the ice used to chill samples, must be autoclaved before disposal Exemplary Materials

- Ice-cold tap water (5 L keep overnight in cold room)
- Conical tubes (sized 15 ml; 50 ml; and 500 ml Corning catalog #431123)
- Cell scraper, length 300 mm, blade 20 mm (TPP catalog #99003)
- Disposable hemacytometer (Kava Glasstic Slide 10 with Grids; catalog #87144)
- Ice-cold Sucrose Flotation Solution
- Ice-cold 0.85% NaCl
- Ice-cold 1.25 M cesium chloride
- PBS with antibiotics (1× Pen/Strep)
- Microcentrifuge at 4° C.
- Large centrifuge 4° C.
- Cole Partner LabGEN 125 Homogenizer with autoclavable Omni Tip plastic tip generator probes 250 and 850 mesh filters and PVC fittings for mesh filters (Bel-Art 378451000 Mini-Sieve Micro Sieve Set)
- small plastic funnels
- Large autoclave tray, or several buckets filled with ice
- 10 L carboy for autoclaving liquid waste Exemplary Procedure Homogenization 1. To a 50 ml conical (With CAP-FILTER), add approximately 35 ml cold water and fecal material collected from several days post infection1. (Day 3-14).
2. Attach a sterile, plastic tip generator probe to an upright, immersion blender (LabGEN 125).
3. While blender is off, submerge homogenizer in contents of conical tube.
4. Blend sample on medium speed until all clumps are broken and a slurry texture is achieved. This may take up to five minutes. Take care to avoid aerosolizing the sample. Place sample on ice and carefully dismantle the blender.

Filtration

5. Assemble the filter apparatus: first insert a 850 μm mesh filter into PVC fitting; place this in the wide side of a funnel, then place the entire apparatus over a 500 ml conical on ice.
6. Slowly pour the homogenized sample over the mesh filter, using a cell scraper to assist the sample to drain through the filter into the conical below.
7. Add approximately 35 ml of cold tap water to the now empty 50 ml conical. Use the cell scraper to gather the solid pieces on top of the mesh, and transfer them back into the conical tube. Shake vigorously.
8. Repeat Steps 6 and 7 for a total f 5-6 times.
9. Remove the mesh filter from the apparatus and replace with a 250 μm mesh filter. It is helpful to use the cell scraper to push the filter out of the PVC fitting from the underside. Reassemble the filter apparatus.

10. Slowly pour the homogenized sample over the mesh filter, using a cell scraper to assist the sample to drain through the filter into the conical below.
11. Add approximately 35 ml of cold tap water to the now empty 50 ml conical. Use the cell scraper to gather the solid pieces on top of the mesh, and transfer them back into the conical tube. Shake vigorously.
12. Repeat Steps 10 and 11 for a total of 3-4 times.
13. Disassemble filter apparatus. Take care to place all components in an autoclavable bin for decontamination at the end of this procedure.

Centrifugation

14. Centrifuge 500 ml conical for 10 minutes at 1000×g at 4° C.
15. Remove supernatant by carefully decanting into 10 L carboy. Resuspend pellet in 50 mL of cold tap water and transfer to a 50 ml conical.
16. Centrifuge sample for 10 minutes at 1000×g at 4° C.
17. Decant supernatant into liquid waste container. Resuspend pellet in 50 ml cold tap water.
18. Split sample into two 50 ml conical tubes, 25 ml in each.

Sucrose Flotation

19. Add 25 mL Sucrose Flotation Solution (1.33 specific gravity) to each conical and mix gently by inverting several times.
20. Immediately centrifuge for 5 minutes at 1000×g at 4° C.
21. After this spin, oocysts are floating in the sucrose solution. Carefully decant entire supernatant from both conicals into a new 500 mL conical to collect oocysts.
22. Add 300 ml cold tap water to the 500 ml conical (should be 400 ml total).
23. Centrifuge 15 minutes at 1500×g at 4° C.
24. Decant supernatant into liquid waste container.
    At this point, oocysts (in pellet) can be resuspended PBS with antibiotics and stored overnight at 4° C. Protocol can be continued the following day.
    Oocysts (in pellet) are resuspended in 5 ml 0.85% NaCl. T Cesium Chloride 25. Add 0.8 ml cold L25 M $CsCl_2$ solution to 10 microcentrifuge tube tubes.
26. Slowly overlay 0.5 ml oocysts from Step 24 (resuspended in 0.85% NaCl) on top of $CsCl_2$ solution in each microcentrifuge tube. Dispense slowly so that two distinct layers are created. Oocysts are floated
27. for a second time during this step separation with $CsCl_2$ layer.
28. Centrifuge for 3 minutes at 16,000×g at 4° C.
29. Remove the top 1 ml of the solution from each microcentrifuge tube and transfer to a new microcentrifuge tube. Oocysts are floating in the supernatant and bacterial contamination and debris will be pelleted. Discard original microcentrifuge tubes with pelleted debris.
30. To microcentrifuge tubes containing floating oocysts, add 0.5 ml 0.85% NaCl. Centrifuge for 3 minutes at 16,000×g at 4° C.
31. Oocysts are now contained in the pelleted material. Discard the supernatant
32. Use 1 ml 85% NaCl to resuspend the pellets each microcentrifuge tube and combine into a single microcentrifuge tube.
33. Centrifuge for 3 minutes at 16,000×g at 4° C. Discard supernatant and resuspend in 1 ml PBS (or water) optionally having antibiotics or in 2.5% potassium dichromate (prepared in ultra-pure water).
34. Remove an aliquot of the purified oocysts, dilute 1:10 in PBS and count on a disposable hemacytometer or use A100 FLR 1× Aqua Glolc-Waterborne inc. Antibody for fast IFA
35. Autoclave all metal and plastic equipment to decontaminate (PVC fittings, metal mesh filters, etc), liquid waste, and contents of ice buckets used to chill solutions and samples.

Reagents and Solutions

Sucrose Flotation. Solution (1.33 specific gravity): 756 g sucrose dissolved in 483 mL deionized water will make approximately 1 liter (3 mL phenol optional). Sucrose at this concentration may take up to 2 hours to dissolve; this solution may be prepared at least a day ahead. Store at 4° C. for up to 6 weeks.

0.85% NaCl: 0.85 g sodium chloride in 100 ml deionized water. Store at 4 OC for up to 2 months.

REFERENCES

Adan et al., *Biosci. Biotechnol. Biochem.*, 6:309 (1999).
Belli et al., 2:456 (2003).
Boothroyd et al., *Philos. Trans. R. Soc. Lund. B. Biol. Sci.*, 352:1347 (1997).
Brown et al., *Appl. Environ. Microbiol.*, 74:18567,
Burg, *J Immunol.* 141:3584 (1988).
Dabritz & Conrad, Zoonoses Public Health, 57:34 (2010).
Donald & Roos, *Proc. Natl. Acad. Sci. USA*, 92:5749 (1995).
Dubey et al., *J. Exp. Med.*, 132:636 (1970).
Dubey et al., *J. Parasitol.*, 97:751 (2011).
Dumètre & Dardè, *J. Microbiol. Methods*, 61:209 (2005).
Fujiwara et al., *BMC Vet Res.* 11:1 (2015).
Guiton et al., *PLoS ONE*. 12:e073018 (2017).
Hall et al., *J. Feline Med. Surg.*, 16:631 (2013).
He et al., 7:e47567 (2012).
Hehl et al., *BMC Genomics*, 16:66 (2015).
Jelińska et al., *J. Pharm. Exp. Therap.*, 287:157 (1_998).
Lujan et al., *Proc. Natl. Acad. Sci.*, 93:7628. (1996).
MacDonald et al., *The Journal of Nutrition*, 113:1422 (1983).
Methods in Molecular Biology DOI 10.1007/7651_2017_1 Springer Science+Business Media New York 2017 Human Intestinal Enteroids: New Models to Study Gastrointestinal Virus Infections
Munera et al., *Cell Stem Cell*, 21:51 (2017).
Navarro et al., *Arterioscler Thromb.*, 12:830 (1992).
Nolan et al., *PLoS Path.*, 13:e1006362 (2017).
Pfaffl, *Nucleic Acids Res.*, 29:2002 (2001).
Pittman et al., *Infect Immun.*, 84:3063 (2016).
Ramakrishnan et al., *Int. J. Parasit.*, 47:597 (2017).
Rivers et al., *Nature*, 258:171 (1975).
Sato et al., *Br. J. Nutr.*, 94:896 (2005).
Schwarz et al., *Mol. Biochem. Parasitol.;* 144:59 (2
Seeber et al., *Gene*, 169:39 (1996).
Shamseddin et al., *Iranian J. Parasitol.*, 10:238 (2015).
Sinclair et al., *Lipids*, 14:932 (1979).
Toledo et al., *Front. Immunol.*, 7:1 (2016)
Trevizan, et al., *Lipids*. 4:23 (2012).
Walker et al., *Genomics.*, 16:1 (2015).
Zulpo et al., *Veterinary Parasitology*. 249:17 (2018).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to generate an immune response to Toxoplasma in livestock, comprising: orally administering to said livestock an effective amount of isolated infectious Toxoplasma oocysts so as to generate an immune response to Toxoplasma, wherein the Toxoplasma oocysts are prepared in vitro.

2. The method of claim 1, wherein the livestock is a sheep, goat or swine.

3. The method of claim 1 wherein the oocysts are resistant to 1% bleach but not to 10% bleach.

4. The method of claim 1 wherein the oocysts are orally, subcutaneously or intraperitoneally administered.

5. The method of claim 1 wherein the oocysts are injected.

6. The method of claim 1, wherein the Toxoplasma is genetically modified to inhibit tachyzoite formation.

* * * * *